United States Patent [19]

Kawasaki

[11] Patent Number: 5,776,422
[45] Date of Patent: Jul. 7, 1998

[54] CLEANING STERILIZATION APPARATUS FOR TOPSOIL

[75] Inventor: Seiji Kawasaki, Yokohama, Japan

[73] Assignee: K. K. Key & Kraft, Tokyo, Japan

[21] Appl. No.: 614,416

[22] Filed: Mar. 12, 1996

[30] Foreign Application Priority Data

Dec. 27, 1995 [JP] Japan .................. 7-341428

[51] Int. Cl.$^6$ .................................................. A01B 77/00
[52] U.S. Cl. .................. 422/307; 43/140; 47/142; 422/308; 422/309
[58] Field of Search ..................... 422/307–309; 47/1.42; 43/140

[56] References Cited

U.S. PATENT DOCUMENTS

| 2,563,926 | 8/1951 | Elliott et al. | 47/1.42 |
| 2,966,128 | 12/1960 | Toulmin | 47/1.42 X |
| 3,443,885 | 5/1969 | Scholtus | 422/307 X |
| 3,802,020 | 4/1974 | Stone et al. | 47/1.42 |
| 4,873,789 | 10/1989 | Plattner | 47/1.42 |
| 5,217,688 | 6/1993 | Von Lersner | 422/309 X |
| 5,406,747 | 4/1995 | Kiefl | 47/1.42 |
| 5,553,414 | 9/1996 | Chapman et al. | 47/1.42 |
| 5,553,415 | 9/1996 | Harvey et al. | 47/1.44 |

FOREIGN PATENT DOCUMENTS

| 64-80203 | 3/1989 | Japan . | |
| 4-13979 | 6/1990 | Japan . | |
| 7-123896 | 5/1995 | Japan . | |
| 626742 | 8/1972 | U.S.S.R. | 42/1.42 |

Primary Examiner—Krisanne Thornton
Attorney, Agent, or Firm—Quarles & Brady

[57] ABSTRACT

A cleaning sterilization apparatus for topsoil which includes: an apparatus body provided with crawlers for traveling over a ground surface and an engine for driving the crawlers; an intake apparatus for taking up the topsoil into the apparatus body; a separating apparatus for removing foreign matters from the soil; a heat sterilization apparatus for thermally sterilizing the topsoil thus separated; and a discharge port constituting for discharging the topsoil sterilized by the heat sterilization apparatus out of the apparatus body; the intake apparatus being provided at a lower portion thereof with an intake port to be moved up and down.

13 Claims, 18 Drawing Sheets

CLEANING STERILIZATION APPARATUS FOR TOPSOIL

BACKGROUND OF THE INVENTION

1. Field of the Invention

The present invention relates to a cleaning sterilization apparatus for topsoil, more particularly to a cleaning sterilization apparatus for thermally sterilizing sand in a sand box court and soil in a crop land and the like.

2. Description of the Invention

The topsoil located in the uppermost portion of the earth has a close relation with a human life. Specifically, a human being communes with nature in his infancy through touch with the soil, and furthermore, the crops are harvested from the crop land. In a sand box court which has been used by children as a playing space, contamination due to excrements of dogs and cats has recently become a problem. Since the children touch the sand directly in such a sand box court, there is a risk that the children are contaminated by coli bacteria or ascarides contained in the sand. Furthermore, there is a danger presented by objects such as a stone, a piece of metal, or a piece of glass mixed in the sand.

On the other hand, in the crop land, when a stone, a piece of metal, or a piece of glass is mixed in the soil, the blades of a cultivator and a sickle thereof may be damaged so that farm work is interrupted. Furthermore, in the crop land, propagation of harmful bacteria in the soil disturbs the growth of the crops, and the influences of disease pests having a soil infectious nature have been a serious problem to replanting that is associated with recent intensive production.

Furthermore, in order to prevent contamination by coli bacteria and ascarides and propagation of bacteria, these being contained in such topsoil, chemical spraying is sometimes carried out. However, with such chemical treatment, the occurrence of a secondary contamination due to chemicals has become a problem. In addition, to remove bacteria and disease pests from the crop land, when chemical spraying is conducted, there has been a fear that useful soil microbes have perished. Moreover, chemical spraying may cause an unevenness of disinfection. It should be appreciated that chemical spraying is harmful to man and animals, and causes damage to crops.

To solve such problems, various methods have been tried, including a steam disinfection method which conducts heating disinfection using a steam pipe, a hot water injection method to inject hot water for thermally disinfection, and a solar heat utilization method to thermally sterilize by solar heat using a vinyl sheet. Any of the above mentioned methods is difficult to automate and is troublesome. Moreover, an unevenness of heating is apt to occur so that efficiency of heating is somewhat diminished.

Furthermore, in Japanese Application Laid Open Heisei 7-123896, a vehicle has been proposed which mounts thereon suction equipment for absorbing sand, heating equipment for heating absorbed sand, separation equipment for removing a dangerous article such as a piece of glass, a cap of an empty can, a nail by sieving the heated sand, and exhaustion equipment for exhausting the purified sand. However, in such a vehicle, the absorption and exhaustion of the sand are carried out by extending a hose to the outside of the vehicle so that heating treatment for the sand can not be performed when the vehicle is running. Hence, the vehicle cannot be used in the crop land. Furthermore, in Japanese Utility Model Application Heisei 4-13979, a soil heating sterilization apparatus has been proposed which comprised a burner for blowing a flame against the soil. However, it can sterilize thermally only the uppermost of the topsoil of the soil. Furthermore, in Japanese Patent Application Laid Open Shouwa 64-80203, soil heating treatment equipment comprises rotary blades located under a portion of a self-driving running body and heating sterilization equipment, located near the rotary blades, for heating the turned over soil. However, such heating sterilization equipment can only turn over the surface of the topsoil. A flame is blown so as to touch directly the topsoil for thermal sterilization, however, an unevenness of heating is apt to occur so that the topsoil can not be thermally sterilized.

SUMMARY OF THE INVENTION

To solve the foregoing problems involved in the conventional art, the major object of the present invention is to provide a cleaning sterilization apparatus for topsoil which is capable of thermally sterilizing topsoil layer of sand or soil, and the like, effectively.

Another object of the present invention is to provide heating sterilization equipment for topsoil which is capable of dipping deeply into the topsoil, and thermally sterilizing during the motion of the apparatus body.

Still another object of the present invention is to provide a heating sterilization equipment for topsoil which is capable of separating impurities from the topsoil as well as thermally sterilizing the topsoil.

The foregoing objects are accomplished in one embodiment by providing a cleaning sterilization apparatus for topsoil comprising an apparatus body having a running and driving mechanism; intake equipment for taking in topsoil into the apparatus body; separation equipment for separating impurities from the topsoil taken in by the intake equipment; heating sterilization equipment for thermally sterilizing the topsoil separated by the separation equipment; and exhausting equipment for exhausting the topsoil thermally sterilized by the heating sterilization equipment into the outside of the apparatus body.

BRIEF DESCRIPTION OF THE DRAWINGS

The preferred embodiments of the present invention will now be described by way of examples with reference to the drawings in which.

DETAILED DESCRIPTION OF THE PREFERRED EMBODIMENTS

Embodiments of the present invention will be described with reference to the accompanying drawings below.

Figure 1:
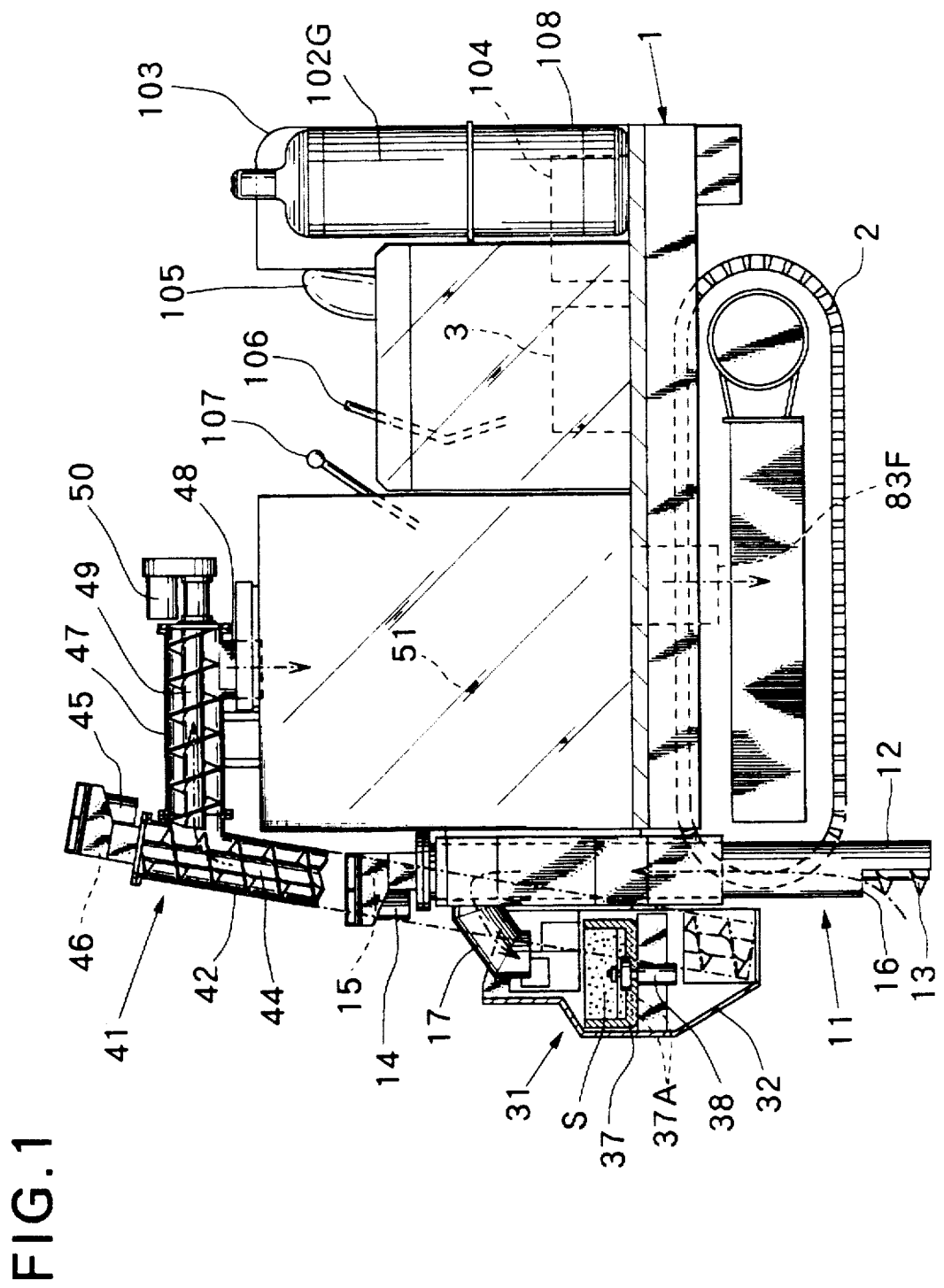
FIG. 1 is a side view partly in section showing a first embodiment of a cleaning sterilization apparatus for topsoil of the present invention.
Figure 8:
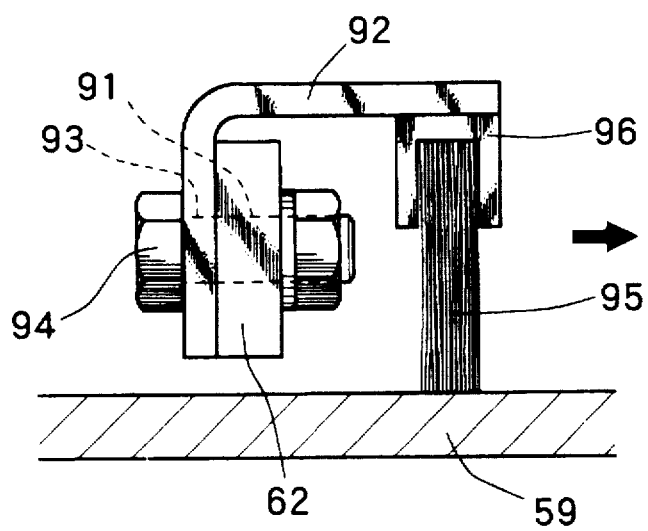
FIG. 8 is a section view of a blade equipped with a brush of the first embodiment of the present invention.

FIGS. 1 and 8 show a first embodiment of the present invention. Referring to the drawings, crawlers 2 are arranged at each side of a lower portion of an apparatus body 1. The crawlers 2 are driven by a running drive means 3, an oil pressure motor or an engine mounted on the apparatus body 1 being used as the running drive means 3.

Figure 2:
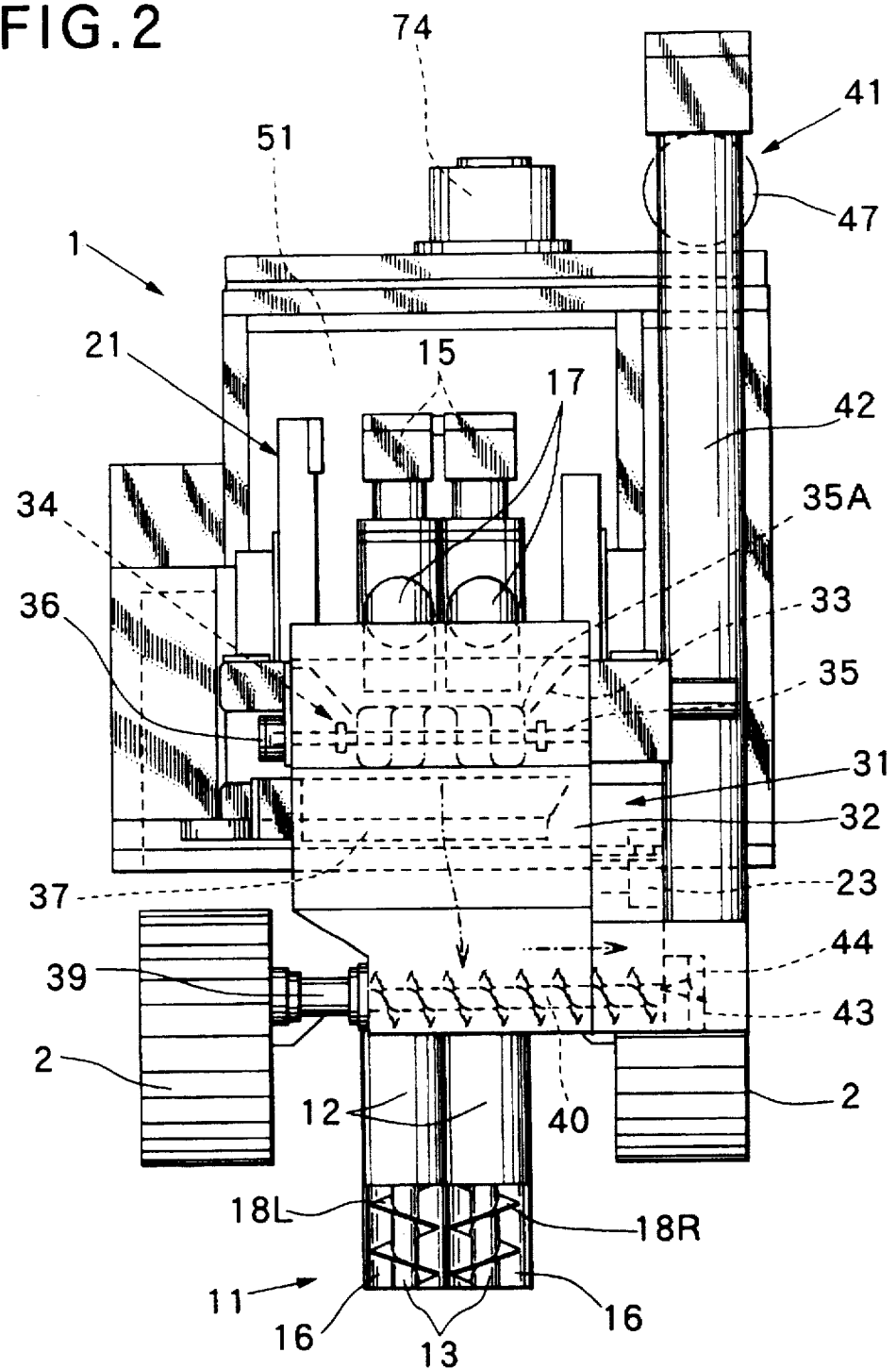
FIG. 2 is a front view showing the first embodiment of the cleaning sterilization apparatus for topsoil of the present invention.
Figure 3:
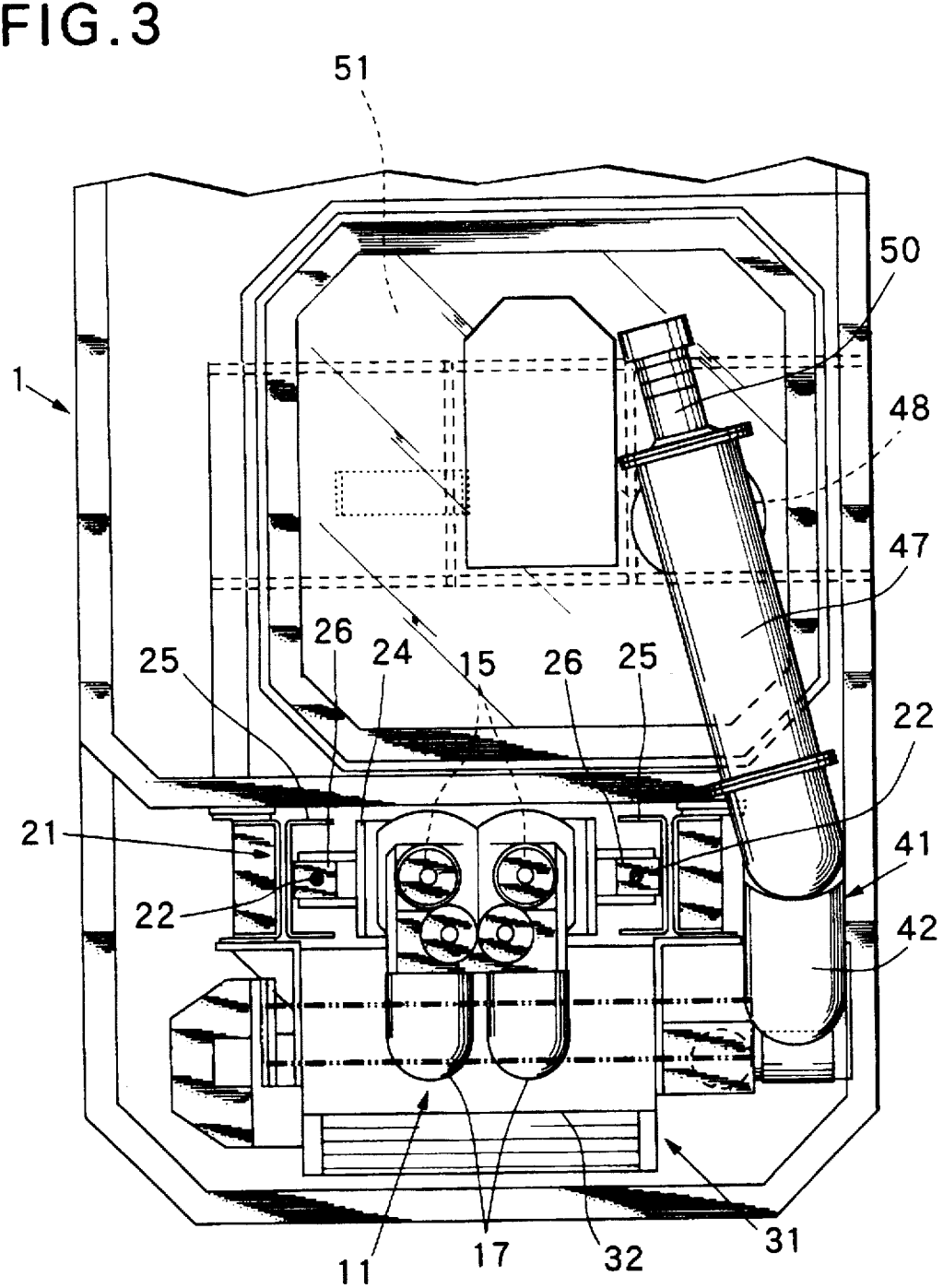
FIG. 3 is a plan view showing the first embodiment of the cleaning sterilization apparatus for topsoil of the present invention.

An intake equipment 11 for taking in topsoil into the inside of the apparatus body 1 is longitudinally at the front portion of the apparatus body 1. The intake equipment 11 comprises an intake screw conveyer 13 in its cylindrical body 12, as shown in FIGS. 1 to 3. The intake screw conveyer 13 is rotatively driven by an intake oil pressure motor 14 disposed in the upper portion of the cylindrical body 12 via a gear group 15. The lowest portion of the cylindrical body 12 is opened and the front portion of the lowest portion of the side wall is opened by approximately one-half thereby forming a topsoil intake port 16. Furthermore, a curved pipe 17 extending downward approximately at a right angle is connected to the rear side at the upper portion of the cylindrical body 12. In this embodiment, the two left and right cylindrical bodies 12 and 12 are provided, and spiral directions of the blade portions 18L and 18R of the screw conveyers 13 and 13 are inverse.

The aforementioned intake equipment 11 is attached to the aforementioned apparatus body 1 via an elevation equipment 21. The elevation equipment 21, as shown in FIGS. 2 and 3, comprises a pair of screw bars 22 located at both sides of the front portion of the apparatus body 1. Each screw bar 22 is fastened to the apparatus body 1, and is supported rotatively by a lower bearing (not shown) in a state where its vertical position is determined. The lowest end of each screw bar 22 is connected to an elevator oil pressure motor 23 fastened to the apparatus body 1, one of which is shown in FIG. 2. A frame-shaped elevating body 24 is located between the pair of the screw bars 22. The elevating body 24 is designed so as to be movable upward and downward along the guide members 25 having the plan shape like a rectangle lacking one side which are arranged at the both sides of the apparatus body 1. The aforementioned intake equipment 11 is fastened to the elevating body 24. Both sides of the elevating body 24 are connected rotatively to the nuts 26 engaged with the aforementioned screw bars 22. Therefore, the aforementioned screw bars 22 rotate by the driving of the aforementioned elevating oil pressure motors 23, and the nuts 26 engaged with these screw bars 22 move upward and downward whereby the aforementioned intake equipment 11 fastened to the elevating body 24 goes up and down. When the intake equipment 11 is at the ascent position, the lowest end of the intake equipment 11 descends to the position touching the earth next to the crawlers 2. When the intake equipment 11 is at the descent position, the lowest end of the intake equipment 11 goes under the ground by about 40 cm. In this situation, the aforementioned intake port 16 is designed such that it disappears under the topsoil completely.

A separation equipment 31 is fastened to the aforementioned apparatus body 1, this equipment 31 being positioned under the opening portion of the lowest end of the aforementioned curved pipe 17 of the aforementioned intake equipment 11. The separation equipment 31, as shown in FIGS. 1 and 2 provides a hopper 33 positioned at an upper portion of a box 32, the upper portion being opened and longer in the left and right directions. The crusher 34 is arranged under the hopper 33 in a horizontal direction. The crusher 34 provides a crushing blade 35A mounted on shaft 35, and provides an oil pressure motor 36 for rotatively driving the aforementioned shaft 35. Furthermore, the separation plate 37 for separating the soil S crushed by the aforementioned crusher 34 is provided. The separation plate 37 is a sieve which is made by perforating a plurality of separation holes 37A through a plate member, or is a sieve using a wire netting as a sieve. Furthermore, the aforementioned separation plate 37 is equipped with a vibration equipment 38, and the aforementioned separation plate 37 is designed such that it is vibrated by the vibration equipment 38. Then, the separation equipment 31 is so designed that the separation plate 37 serving as a sieve separates the impurities from the soil or it separates the clod, which could not be crushed by the aforementioned crusher 33, from the crushed soil. Furthermore, the screw conveyor 40 rotatively driven by the oil pressure motor 39 is arranged at the lower portion within the aforementioned box 32, and the injection equipment 41 having the lowest end facing the conveying terminal of the screw conveyor 40 is arranged.

As shown in FIG. 1, in the injection equipment 41, its longitudinal cylindrical body 42 is fastened to the aforementioned body 1, and the suction port 43 formed at the lowest end of the cylindrical body 42 is located at the left side of the screw conveyor 40. The injection equipment 41 comprises the suction screw conveyor 44 in the cylindrical body 42, and the suction screw conveyor 44 is rotatively driven by the suction oil pressure motor 45, which is formed in the upper portion of the cylindrical body 42, via the gear group 46. In the injection equipment 41, one terminal of the conveyance pipe 47 extending in a horizontal direction is connected to the rear surface of the upper portion of the cylindrical body 42, and the injection pipe 48 is connected to the lower surface of the other end of the conveyance pipe 47. Furthermore, the screw conveyor 49 is arranged in the conveyance pipe 47, and the screw conveyor is rotatively driven by the convey oil pressure motor 50 arranged in the other end of the conveyance pipe 47. Therefore, the soil S is conveyed to the conveyance pipe 47 by the suction screw conveyor 44, and is further conveyed to the injection pipe 48 by the screw conveyor 49. Then, the soil S falls down from the lowest end of the injection pipe 48.

Figure 4:
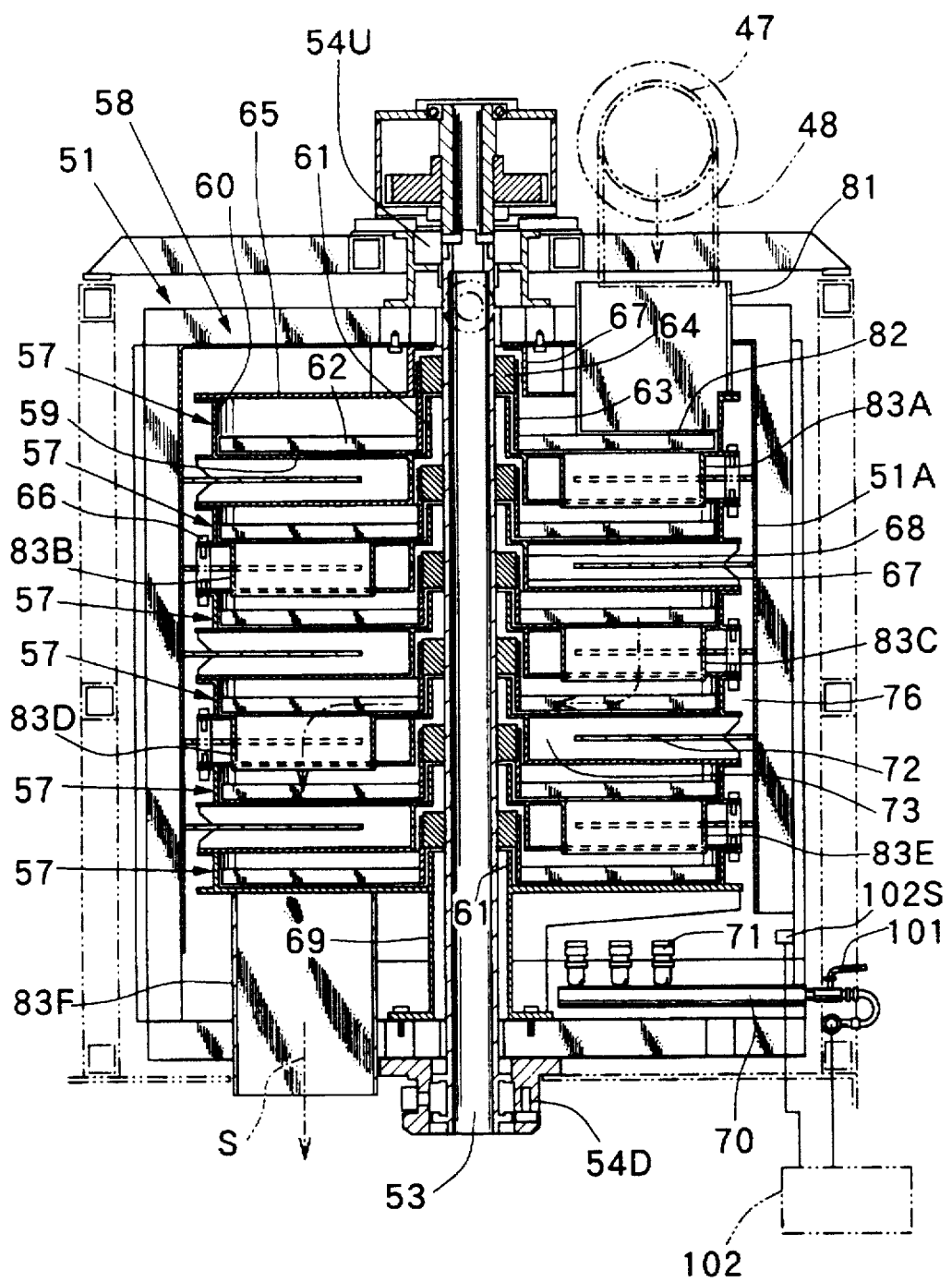
FIG. 4 is a section view showing the first embodiment of the heating sterilization equipment for topsoil of the present invention.
Figure 5:
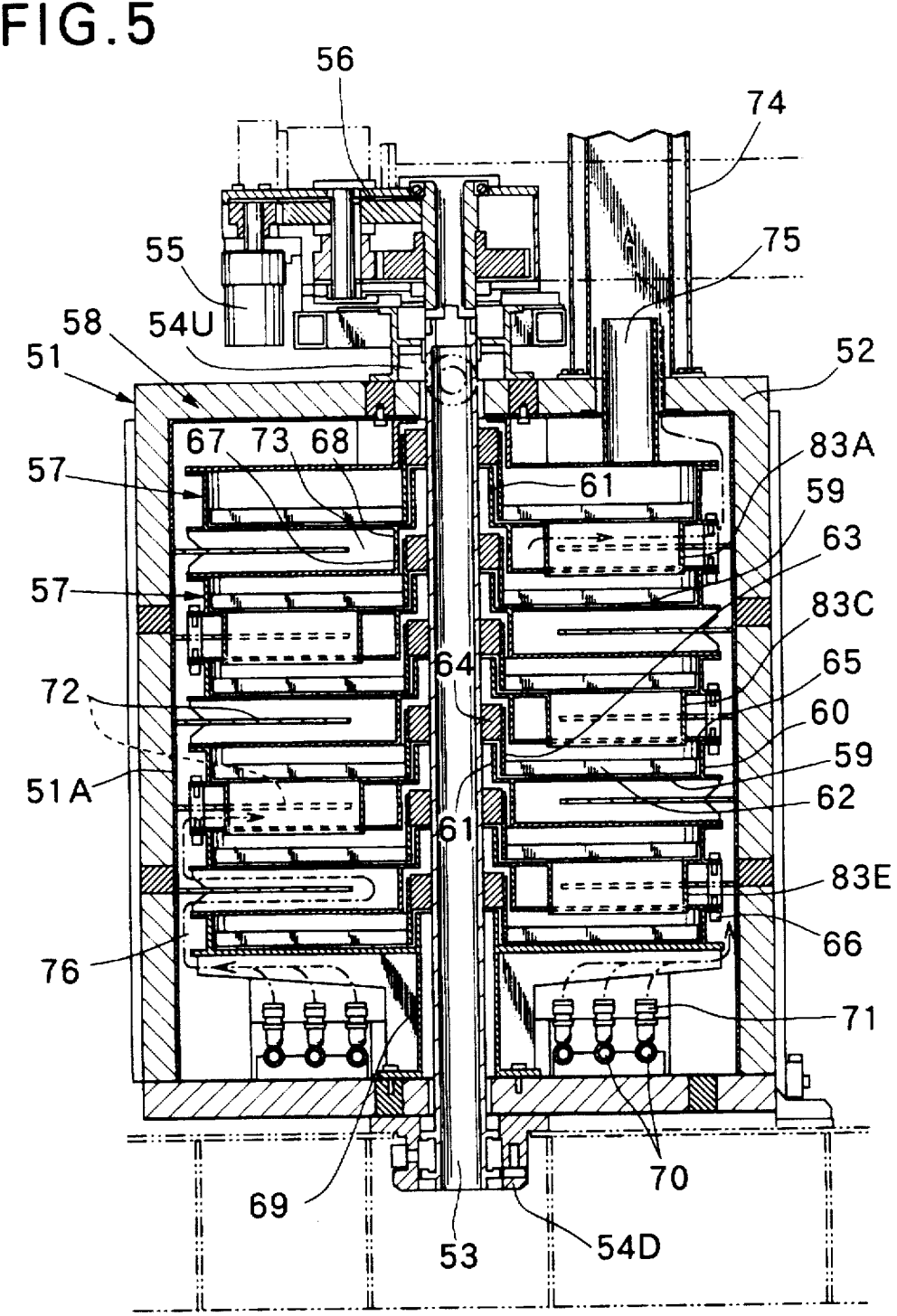
FIG. 5 is a section view showing the first embodiment of the heating sterilization equipment for topsoil of the present invention.

As shown in FIGS. 4 and 5, in the apparatus body 1, the heating chamber 51 is cylindrical inside. The heat insulating material 52 covers the upper surface, lower surface, and outer surface of the heating chamber 51. The central axis 53 serving as a rotation axis is arranged at the center of the heating chamber 51, and the central axis is supported rotatively by the bearings 54U and 54D arranged at the lower and upper portions of the aforementioned apparatus body 1. The thrust bearing is used at least for the bearing 54D, the rotation oil pressure motor 55 serving as the central axis rotation means is arranged at the upper portion of the central axis 53, and the central axis 53 is rotatively driven by the rotation oil pressure motor 55 via the gear group 56.

In the aforementioned heating chamber 51, a plurality of approximately cylindrical-shaped topsoil heating chambers (hereinafter referred to as heating compartments 57) are arranged at intervals in a vertical direction, and a heating sterilization equipment 58 is constituted of the heating compartments 57 and a heating equipment described later. In this embodiment, the heating compartments 57 are arranged at six stages. Each of the heating compartments 57 comprises the heating plate 59 formed of a comparatively thin plate, the outer cylinder portion 60 arranged at the outer circumference side of the heating plate 59, and the inner cylinder portion 61 rotatively at the central side of the heating plate 59 and inserted into the aforementioned central axis 53 in a loosely connected state. The heating compartment 57 is fixed to the heating sterilization equipment 58. Furthermore, the blade 62 formed of a plate piece is arranged rotatively along the upper surface of the heating plate 59, and the base portion of the blade 62 is fixed to the lower portion of the outer circumference of the cylindrical fixing portion 63 serving as an erect portion. The cylindrical fixing portion 63 is inserted into the outer circumference of the inner cylinder portion 61 for rotation, and the upper portion of the cylindrical fixing portion 63 is fixed to the fixing ring 64. The fixing ring 64 is fixed to the aforementioned central axis 53 whereby the plurality of the blades 62 are radially arranged. It is noted that the eight blades 62 are spaced equally around the circumference of the central axis 53 in this embodiment. Furthermore, the ring-shaped cover 65 is arranged at the upper portion of the aforementioned heating compartment 57, and the cover is fixed to the flange portion 60A located at the upper portion of the aforementioned outer cylinder portion 60 with the fixing member 66 such as a bolt. In close vicinity to the cylindrical fixing portion 63, the upper cylinder portion 67 is arranged at the center of the cover 65. The lower cylinder portion 68 is arranged in a downward direction on the under surface of the heating plate 59 corresponding to the upper cylindrical portion 67. Thus, the upper and lower cylindrical portions 67 and 68 face each other. The uppermost end of the upper cylindrical portion 67 of the uppermost cover 65 is fixed to the upper surface of the heating chamber 51. The cylindrical foot portion 69 is hanged from the lower portion of the upper cylindrical portion 67 which is the lowermost one among the upper cylindrical portions. The lower portion of the cylindrical foot portion 69 is fixed to the lower surface of the aforementioned heating chamber 51. Furthermore, the aforementioned heating compartment 57 and the blade 62 are formed of stainless steel. A plurality of gas burner fixing pipes 70 extending in a horizontal direction are arranged at the lower portion within the aforementioned heating chamber 51 in parallel with each other. The fixing pipes 70 are formed of a stainless steel pipe, and comprises a plurality of gas burners 71 serving as a heating equipment. Furthermore, the aforementioned upper and lower heating compartments 57 are divided from each other by the ring-shaped divider plate 72. The outer circumference of the divider plate 72 is contacted to the inner surface 51A of the aforementioned heating chamber 51 to be fixed thereto without any gap. The hot air hole 73 in a longitudinal direction is arranged between the central opening of the divider plate 72 and the upper and lower cylinder portions 67 and 68. Furthermore, the funnel 74 connecting to the inside of the heating chamber 51 is arranged on the upper surface of the aforementioned apparatus body 1, the funnel 74 standing upwardly. The upper portion of the regulation cylinder 75 standing longitudinally on the uppermost cover 65 is inserted into the lower portion of the funnel 74. Therefore, when the aforementioned burner 71 is fired, the hot air passes through the hot air path 76 designed such that the hot air is exhausted to the outside from the upper funnel 74 in the following manner. Specifically, the hot air caused by the flame of the burner tends to the outer circumference of the lower surface of the uppermost heating plate 59, and flows up through the gap between the outer circumference of the heating compartment 57 and the inner surface of the heating chamber. Then, the hot air tends in a central direction through the divider plate 72 and the cover 65, flows up through the central hot air hole 73, and tends in a outer direction through the heating plate 59 and the divider plate 72. Subsequently, the hot air flows up through the gap between the outer circumference of the heating compartment 57 and the inner surface of the heating chamber 51, the heating compartment 57 being located in the secondary stage from the bottom. The hot air passes through the central hot air hole 73 by the divider plate 72 of the secondary stage. The hot air travels in each stage in the same manner. In this manner, a hot air passage 76 is formed starting from the lowermost heating plate 59 to the funnel 74 disposed at the uppermost portion of the heating chamber 51 for exhausting the heating air.

Figure 6:
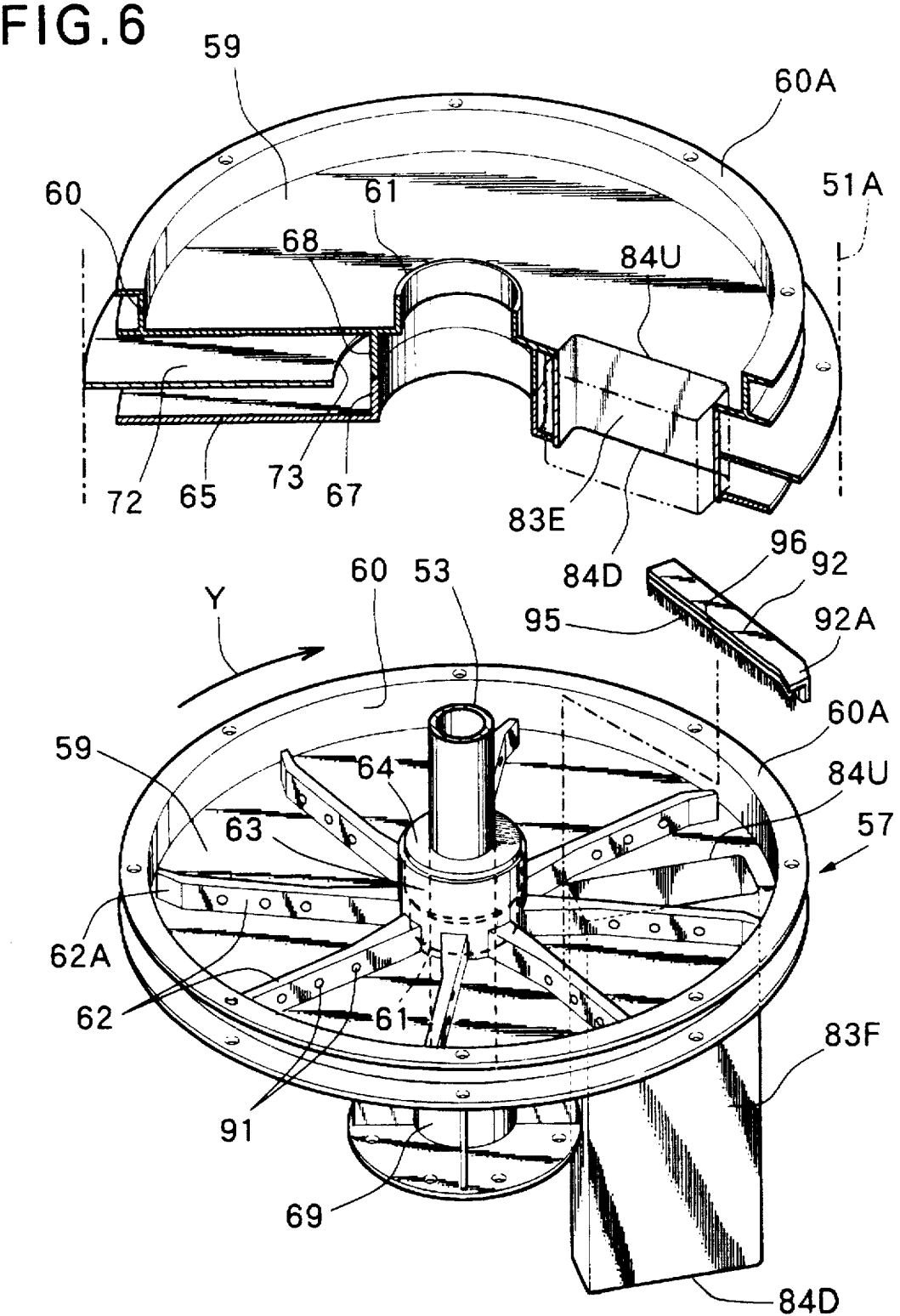
FIG. 6 is an exploded perspective view of a topsoil heating compartment showing the first embodiment of the present invention.
Figure 7:
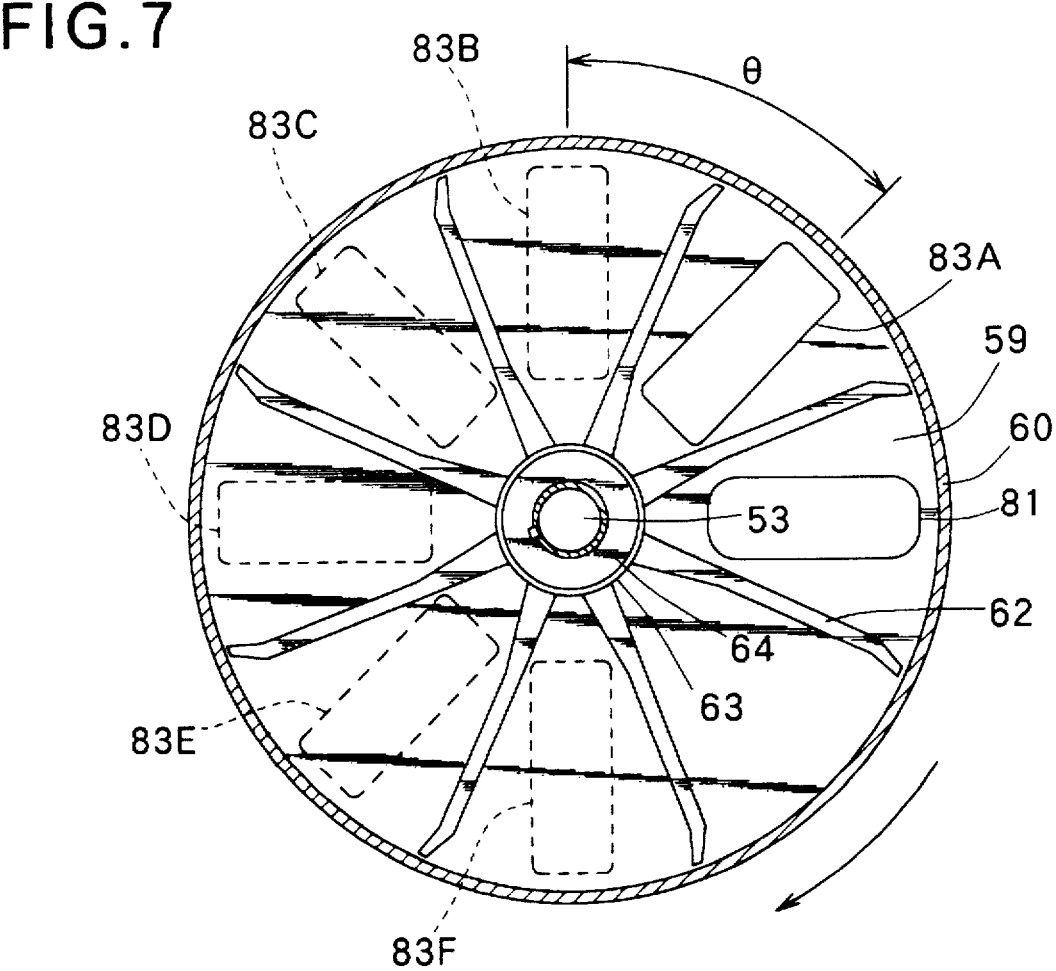
FIG. 7 is a plan view of a blade illustrating exit ports of the first embodiment of the present invention.

Further, as shown in FIGS. 4 and 5, the apparatus body is provided with a cylindrical injection port 81 to align with the injection pipe 48 so as to communicate with the interior of the heating chamber 51. The lower portion of the injection port 81 is protruded through a portion of the uppermost cover 65 into the uppermost heating compartment 57. A scraper 82 is mounted on the lower portion of the injection port 81, and the lower end of the scraper 82 is disposed near the upper edge portion of the blade 62. The heating plate 59 at each stage is provided respectively with cylindrical dropping ports 83A, 83B, 83C, 83D, 83E and 83F, and the lower end portion of each of the cylindrical dropping ports 83A, 83B, 83C, 83D, 83E and 83F is penetrated through each underlying cover 65 so as to communicate with the heating compartment 57 of the next lower stage. Thus, the dropping port 83F constitutes an exhaustion port and the lower end portion of the dropping port 83F is protruded out from the bottom of the heating chamber 51. In FIGS. 4 and 5, the cylindrical dropping ports 83A, 83B, 83C, 83D, 83E and 83F are alternately arranged on both sides, i.e. left and right, for the convenience of explanation. However, these dropping ports 83A, 83B, 83C, 83D, 83E and 83F are actually arranged as shown in FIG. 7. In FIG. 6, the arrow "Y" illustrates the rotational direction of the blades 62, and the dropping port 83A of the uppermost stage is positioned at the most downstream side of the rotational direction of the blade as viewed in relation to the position of the injection port 81. The dropping port 83B is disposed next to and at the upstream side of the dropping port 83A as viewed in the rotational direction of the blade. Likewise, any dropping port of lower stage is disposed next to and at the upstream side of the dropping port of upper stage as viewed in the rotational direction of the blade. The lowermost dropping port 83F constituting an exhaustion port is disposed next to and at the upstream side of the dropping port 83E of the second last stage as viewed in the rotational direction of the blade. Each of the dropping ports 83A, 83B, 83C, 83D, 83E and 83F is provided with a rectangular upper and lower openings 84U and 84D each being elongated in the radial direction from the center of central axis 53. The opening area of each of the upper and lower openings 84U and 84D is made smaller than each area portion of the heating plate 59 partitioned by a pair of the neighboring blades 62. The lower opening of the injection port 81 is also elongated in the radial direction from the center of central axis 53, and at the same time has an area which is smaller than each area portion of the heating plate 59 partitioned by a pair of the neighboring blades 62. FIG. 7 shows a plan view of the heating plates 59 wherein the injection port 81 and the dropping ports 83A, 83B, 83C, 83D, 83E and 83F are equidistantly spaced apart from each other by an angle "θ" of 45 degrees so as to correspond with the partitioned regions of the heating plate 59 which are formed between the neighboring blades 62. However, it is also possible to change the angle "θ" to lower than 45 degrees so as to allow the space between the neighboring ports to become closer to each other provided that any of the injection port 81 and the dropping ports 83A, 83B, 83C, 83D, 83E and 83F would not overlap with the neighboring ports.

The distal end portion 62A of the blade 62 is bent toward the rotational direction of the blade, and a plurality of fixing holes 91 are formed in each blade 62 as shown in FIGS. 6 and 8. On the other hand, an adaptor 92 such as an angle member provided with a plurality of fixing holes 93 is firmly secured to the blade 62 by means of a securing member 94 such as bolts and nuts, and then a stainless steel brush as a sliding member is mounted at the top edge portion of the adaptor 92. The upper portion of the brush 95 is held by a holding member 96 fusion-bonded to the lower surface of the top edge portion of the adaptor 92. In this manner, the brush 95 having substantially the same length as that of blade 62 is placed on the forward side; in the rotational direction, of the blade 62 and slides on the upper surface of the heating plate 59. The distal end portion 92A of the adaptor 92 is also bent toward the rotational direction of the blade and likewise the distal end portion of the brush 95 is also bent toward the rotational direction of the blade. When the brush 95 is to be employed, the scraper 82 is placed near the upper portion of the adaptor 92. This brush may be mounted at the rear side, in the rotational direction, of the blade 62. In this case also, the earth "S" that may be left on the heating plate 59 after the rotation of the blade 62 can be effectively moved away.

A switching valve 101 is mounted at the proximal end portion of the gas burner fixing pipe 70, and is controlled by a heat control apparatus 102 mounted on the apparatus body 1. This heat control apparatus 102 is connected with a gas (for example, LPG) cylinder 102G and further connected electrically with a temperature sensor 102S mounted in the heating chamber 51. With this heat control apparatus 102, the ignition and extinction of the gas burner 71 is carried out. The temperature within the heating chamber 51 is measured by the temperature sensor 102S in order to control the flow rate and pressure of the gas to be supplied to the gas burner 71, thus controlling the temperature of the heating plate 59 to a predetermined range. An oil tank 103 is mounted on the rear portion of the apparatus body 1, the oil tank 103 being connected with an oil-controlling apparatus 104 so as to control the operations of each of the oil pressure motors 14, 23, 36, 39, 45, 50 and 55. A seat 105 for an operator is provided on the rear portion of the apparatus body 1. An engine throttle 106 and a travel lever for operating the traveling direction of the apparatus body 1 through the crawler 2 are positioned beside the seat 105. A fuel tank 108 for the engine 3 is mounted on the rear portion of the apparatus body 1.

Next, the method of operating the cleaning sterilization apparatus as described above will be explained. This cleaning sterilization apparatus is adapted to automatically carry out the sterilization of the topsoil in a sand box court or farm land. First of all, the elevation equipment 21 is actuated to lower the elevating body 24 so as to insert the intake port 16 into the soil "S" at a predetermined depth. When the soil is to be taken up in this manner, the intake port 16 can be lowered to a desired position which is lower than the crawlers 2, but when the apparatus body 1 is in the normal traveling state, the intake apparatus 11 can be sufficiently raised to avoid disturbing the traveling of the apparatus body. Then, the apparatus body 1 is allowed to travel forward by means of the crawler 2 so as to take up the soil "S" from the intake port 16 by actuating the intake apparatus 11, and at the same time the intake screw conveyors 13 disposed on both sides are allowed to move upward for carrying the soil up to the curved pipe 17 from which the soil is allowed to fall down into the separating apparatus 31. In this case, as shown in FIG. 2, since the vanes 18R and 18L of the intake screw conveyors 13 are spirally formed in the opposite direction from each other and the intake screw conveyors 13 rotate in the opposite direction from each other, the vanes 18R and 18L are caused to rotate in the same speed with each other but in opposite directions from each other. As result, the rotational resistance of the intake screw conveyors 13 is well balanced, thereby allowing the apparatus body 1 to stably travel in the straight direction. The amount of soil to be taken up by the intake port 16 can be adjusted by adjusting the height of the intake apparatus 11 by actuating the elevation equipment 21 and at the same time by adjusting the rotational speed per unit time of the screw conveyors 13. The soil "S" discharged from the curved pipe 17 falls in the hopper 33 as shown in FIGS. 1 and 2, and is then crushed by the rotating crushing blades 35A disposed below the hopper 33. The soil thus crushed is then allowed to fall onto the separating plate 37 vibrating by means of the vibrator 38, the soil passed through the separating meshes 37A of the separating plate 37 is allowed to fall downward, and the foreign matter such as small stones and pieces of glass or large solids which are left on the separating plate 37 are removed. Since the separating plate 37 is caused to vibrate by the vibrating apparatus 38, the clogging of the separating meshes 37A during the separating operation by the separating plate 37 can be avoided. The soil thus separated from foreign matter or solids larger than a predetermined size is transferred via screw conveyor 40 disposed at the lower portion of the box 32 toward the suction port 43 of the injection apparatus 41.

The soil "S" separated from foreign matter by means of the separating apparatus 31 is further transferred upward by means of the suction screw conveyor 44 from the suction port 43 of the injection apparatus 41 shown in FIG. 2, and then allowed to fall onto the injection pipe 48 by means of the transfer screw conveyor 49. The soil "S" falling on the uppermost heating plate 59 from the injection port 81 disposed below the injection pipe 48 is transferred as a relatively thin layer, the height of which is almost the same as that of the blade 62, onto the heating plate 59 while avoiding the soil from being accumulated higher than the height of the blades by the cutting action of the scraper 82, since the scraper 82 is disposed proximate to the upper edge of the blade 62. The soil "S" is then thermally sterilized by the heat from the heating plate 59 while the soil is being moved via the blade 62 to the dropping port 83A positioned at the most downstream side of the rotational direction of the blade as viewed relative to the position of the injection port 81. Since the heating plate 59 having a relatively large area is heated, and the soil is heated while being transferred as a relatively thin layer on this heating plate 59, the heat transfer coefficient between the heating plate 59 and the soil can be improved, so that the soil layer as a whole can be effectively heated. Further, the soil "S" falling from the dropping port 83A of the uppermost stage is then positioned on the surface of another heating plate 59 of lower stage, and thermally sterilized while being moved to make almost a round of this heating plate 59 until it falls from the dropping port 83B. The soil "S" from the dropping port 83B falls on the heating plate 59 of lower stage and is thermally sterilized in the same manner as explained above and transferred to the lower heating plate 59. After repeating the same processes as mentioned above, the soil is finally allowed to be discharged from the dropping port 83F to the lower portion of the apparatus body 1.

The hot air including any flame generated from the gas burner 71 heats the heating plate 59 and flows toward the outer periphery of the heat plate 59 of the lowermost stage and then ascends through a space between the outer periphery of the heating compartment 57 and the inner wall of the heating chamber 51. The hot air thus ascended moves through a space between the divider plate 72 and cover 65 toward the center portion of the apparatus body 1, and then further ascends through the central hot air hole 73. Thereafter, the hot air moves via a space between the heating plate 59 and the divider plate 72 toward the outer region of the apparatus body and ascends through a space between the outer periphery of the heating compartment 57 of the second stage and the inner wall of the heating chamber 51. The hot air is then forced to pass through the hot air hole 73 due to the presence of the divider plate 72 of the second stage, and, after passing through each of the upper stages in the same manner as explained above, discharged from the funnel 74. Since the hot air passes through a labyrinth type hot air passage 76 formed along the outer wall of the heating compartment 57, heat from the hot air can be effectively transmitted to the heating plate 59. The adjustments regarding to the treating volume and heating temperature of the soil "S" can be effected by controlling the rotational speed of the blades 62 and by controlling the number of the gas burners 71 that are actuated by the heat control apparatus 102 respectively. Since the top of the heating compartment 57 is closed by the cover 65, the soil would not be directly contacted by the flame from the gas burner 71. Further, due to the provisions of the upper and lower cylindrical members 67, 68 and the cylindrical leg portion 69, the hot air does not diffuse toward the central axis 53.

The soil "S" being transferred by the rotation of the blade 62 can be effectively prevented from falling into a region around the central axis 53 due to the provision of the inner cylindrical member 61 disposed proximate to the center of the heating compartment 57. The soil "S" transferred onto the space between the blade 62 and the heating plate 59 can be effectively wiped away by the brush 95 mounted on the forward side (in rotational direction) of the blade 62. The heat control apparatus 102 heats the soil "S" to a predetermined temperature while controlling the flow rate and pressure of gas to be supplied to the gas burners 71 and the number of gas burners 71 that are ignited. When the temperature is raised higher than the preset temperature, the on-off control of the gas supply is operated. In this case, since the heating by the heat control apparatus 102 is confined to the interior of the heating chamber 51 covered with a heat-insulating material 52, it is possible to achieve an excellent thermal efficiency and to prevent an increase in temperature of the external portion of the apparatus body 1. The soil "S" thus thermally sterilized is then discharged from the dropping port 83F disposed at the lower portion of the apparatus body 1. Since the soil "S" taken up by the intake apparatus 11 mounted at the forward central portion of apparatus body 1 is discharged from the central lower portion of the apparatus body 1, substantial leveling of soil after finishing the sterilization of the soil in the sand box court or farm land would not be required.

As explained above, according to this example, the cleaning sterilization apparatus for topsoil comprises the apparatus body 1 provided with the running drive means 3, the intake apparatus 11 for take-up the topsoil such as sand and soil "S" into the apparatus body 1, a separating apparatus 31 for separating the foreign matter from the soil taken up by the intake apparatus 11, the heat sterilization apparatus 58 for thermally sterilizing the soil "S" separated by the separating apparatus 31, and the dropping port 83F constituting a discharging port for discharging the soil "S" sterilized by the heat sterilization apparatus 58 out of the apparatus body 1. The heat sterilization apparatus 58 comprises the cylindrical heating compartment 57 provided at its bottom with the heating plate 59, the central axis 53 erected at the center of the heating plate 59, the blades 62 radially extended from the central axis 53 and adapted to rotate over the upper surface of the heating plate 59, the oil pressure motor 55 for rotating the blades 62, and the gas burners 71 for heating the heating plate 62. According to this cleaning sterilization apparatus, a topsoil such as sand or soil "S" is taken up into the apparatus body 1 while the cleaning sterilization apparatus is driven to travel by the running drive means 3, and the topsoil thus taken into the apparatus body 1 is subjected to the separation process in the separating apparatus 31 thereby removing any foreign matter from the topsoil, and the soil thus separated is then thermally sterilized in the heat sterilization apparatus 58, the sterilized soil being discharged from the dropping port 83F. These treatments are automatically carried out according to this cleaning sterilization apparatus. In the sterilization apparatus 58, the heating plate 59 is heated by the gas burners 71, and the blades 62 are driven by the oil pressure motor 55 to rotate along the upper surface of the heating plate 59 to cause the soil to move over the upper surface of the heated heating plate 59. In this case, since the soil is caused to move over the upper surface of relatively wide area of the heating plate 59, the heat of the heating plate 59 can be effectively transmitted to the soil moving thereon. Further, since the topsoil is thermally sterilized instead of being chemically sterilized through the use of chemicals, any possibility of secondary contamination can be avoided. With this thermal sterilization, any harmful microorganisms such as coli bacteria, eggs of ascarides and other bacteria contained in the topsoil can be effectively removed. Therefore, this cleaning sterilization apparatus is very well suited for use in treating the topsoil in a farm land for cultivating field crop. Moreover, since the small stones or pieces of glass contained in the topsoil can be effectively removed in concurrent with the thermal sterilization, this cleaning sterilization apparatus is also suited for use in treating the topsoil in a sand box court, thus assuring the safety of children playing in the sand box court. When this cleaning sterilization apparatus is employed in treating a crop land, damage to the rotary vane of a cultivator or damage to a sickle due to the small stones or pieces of glass contained in the topsoil can be avoided, thus assuring a safe farm working. Moreover, since the apparatus body 1 is of self-mobile type, a load on the operator can be alleviated. Furthermore, since the soil "S" is taken up by the screw conveyor 13 of the intake apparatus 11, and then treated, the screw conveyor 13 acts also as a cultivator, i.e. the topsoil can be relatively deeply cultivated by the screw conveyor 13 thus supplying oxygen into the farm land and thereby activating the aerobes in the topsoil concurrent with the thermal sterilization treatment.

According to this example, since the blade 62 is provided with a brush 95 which is adapted to slide over the heating plate 59 so as to wipe away sand or soil "S" on the heating plate 59, there is little possibility that the space between the blade 62 and the heating plate 59 is clogged with small stones or other solid materials. Namely, in a construction where metallic blades 62 are rotatably mounted in close to the upper surface of the metallic heating plate 59, a gap is inevitably formed between the metallic blades 62 and the metallic heating plate 59, because of an error in manufacture of these components, an error in mounting these components, a thermal deformation or a clearance required between these components, so that there is a possibility that the gap between the blade 62 and the heating plate 59 is more likely to be clogged with small stones and the like contained in the soil, thus raising a trouble of stopping the rotation of the blades. However, since the brush 95 is mounted on the blades 62 in this invention so as to wipe away the soil remaining on the heating plate 59, it has become possible to stably rotate the blades 62.

Additionally, according to this example, a plurality of heating compartments 57 are superimposed one upon another in plural stages with some space formed therebetween. At the same time the dropping port 83A is formed in the heating plate 59 of the uppermost heating compartment 57 and the gas burners 71 are disposed below the lowermost heating compartment 57. Then the soil "S" can be thermally sterilized while the soil "S" is transferred over the uppermost heating plate 59 to the dropping port 83A, and the soil falling from the dropping port 83A is then further thermally sterilized successively while the soil is transferred over the lower heating plates 59 mounted in plural stages, thereby performing an effective sterilization of the soil. Moreover, since the superimposed heating compartments 57 are heated by the gas burners 71 mounted at the lower portion of the apparatus body, the simplification of heating means can be achieved.

Further, according to this example, the heating plate 59 is provided at the center thereof with the inner cylinder 61 coaxially mounted around the central axis 53, and the cylindrical fixing member 63 as an erect member is attached to the proximal portion of the blades 62, the upper portion of the cylindrical fixing member 63 being fixed to the central axis 53. The central axis 53 is adapted to be rotated by the oil pressure motor 55, so that the blades 62 of all stages are also rotated by the oil pressure motor 55 together with the rotation of the central axis 53. Due to the presence of the inner cylindrical member 61, the soil "S" on the heating plate 59 would not fall down toward the central axis 53 from the heating plate 59 thus assuring the stable rotation of the central axis 53.

Since the intake port 16 is mounted at the lower portion of the intake apparatus 11 in such a manner as to be moved up and down, the topsoil of desired depth can be taken up by adjusting the height of the intake port 16. When the apparatus body 1 is stored or in the normal traveling state, the intake apparatus 11 can be raised, thus avoiding any disturbance to the transportation and movement of the apparatus body. Since the crusher 34 for crushing the soil "S" that is taken up is mounted on the apparatus body 1, the mass of soil can be effectively crushed so as to facilitate the separating treatment by the separating plate 37. Further, the vibrating apparatus 36 for vibrating the separating plate 37 of the separating apparatus 31 is mounted on the apparatus body 1, so that the separation between the foreign matters and soil "S" can be effectively carried out. Further, the scraper 82 is disposed close to the upper edge of the blade 62 at the injection port 81 for injecting the soil into the uppermost heating compartment 57, so that the height of the layer of the soil "S" to be supplied to the heating plate 59 can be lowered to a suitable height by the cutting action of the scraper 82. In each of the plurality of the heating compartments 57 mounted in a plurality of stages, the dropping ports 83A, 83B, 83C, 83D, 83E and 83F for discharging the soil "S" are respectively disposed at the upstream side in the rotational direction of the blades 59 in relation to each of the injection port 81 and the dropping ports 83A, 83B, 83C, 83D, 83E, the soil is allowed to make almost a round of each heating plate 59, thus making it possible to perform an effective sterilization. Each of the injection port 81 and the dropping ports 83A, 83B, 83C, 83D, 83E and 83F is shaped into a rectangular form elongated in the radial direction from the center of central axis 53, and the length thereof is nearly a half of the radius of the heating plate 59, so that the soil from the upper stage will be allowed to fall uniformly in the radial direction of the heating plate 59, and at the same time the soil on the heating plate 59 can be almost completely dropped to the heating plate 59 of the next lower stage. Since the brush 95 is mounted on the forward side, in the rotational direction, of the blade 62 to wipe away the soil before the blade 62, the intrusion of the small stones into and below the blade 62 can be effectively prevented. Further, since the distal end portion 62A of the blade 62 is bent somewhat in the rotational direction of the blade 62, the soil on the outer circumference of the heating plate 59 can be moved toward the center of the heating plate 59. Since the apparatus body 1 is provided with the gas cylinder 102G, the oil tank 103 and the fuel tank 108, the apparatus body 1 as well as the various devices mounted on the apparatus body 1 can be operated without requiring an external motive power. Further, since a space is provided between the heating compartments 57 disposed one upon another, since a divider plate 72 is provided for partitioning one heating compartment 57 from another heating compartment 57, and since a hot air hole 73 is formed at the center of the divider plate 72, the heat from the gas burners 71 is forced to pass through the hot air passage 76 of labyrinth type comprising the repetitions of the bottom surface of heating plate 59, the upper surface of the outer circumference portion 67, the upper surface of the cover 65 and the hot air hole 73. Therefore, each of the heating plates 59 disposed in each stage can be effectively heated by the gas burners 71 disposed at the lower portion of the apparatus body 1. Furthermore, since the upper portion of the heating compartment 57 is closed by the cover 65, the soil would not be directly touched by the flame of the gas burners 71, so that useful microorganism contained in the soil would not be perished. Due to the provisions of the upper and lower cylindrical members 67, 68 and the cylindrical leg portion 69, the hot air would not diffuse toward the central axis 53, and hence the heat from the gas burner 71 can be consumed for heating the heating plate 59 without wasting the heat. Moreover, since the central axis 53, a set of gears 56 and the oil pressure motor 55 for rotating the blades are not exposed to the hot air, the stable rotation of these components can be assured. The temperature within the heating chamber 51 is measured by the temperature sensor 102S, and the flow rate and pressure of the gas to be supplied to the gas burners 71 are controlled on the basis of the measured result, so that the topsoil can be thermally sterilized at a desired temperature, thus making it possible to control the heating temperature depending on the kinds of the bacteria, bacillus or eggs of ascarides to be killed. Therefore, it is possible to selectively sterilize the soil by only killing harmful bacteria.

Since the intake apparatus 11 is mounted at the forward central portion of apparatus body 1, and the dropping port 83F for discharging the sterilized soil is mounted at the central lower portion of the apparatus body 1, substantial leveling of sterilized soil after the return of the soil back to the sand box court or farm land would not be required. The bearings 54U and 54D as well as a set of gears 56 for transmitting the rotation of the oil pressure motor 55 are mounted outside the heating chamber 51 so as to prevent these components from being exposed to the heat from the heating chamber 51, and to assure the stable rotation of these components for a long period of time. Since the upper portion of the regulation cylinder 75 is inserted into the lower portion of the funnel 74 so as to permit the exhaustion of gas from the space between the funnel 74 and the regulation cylinder 75, it has become possible to inhibit the escape of the heat from inside the heating chamber 51.

Figure 9:
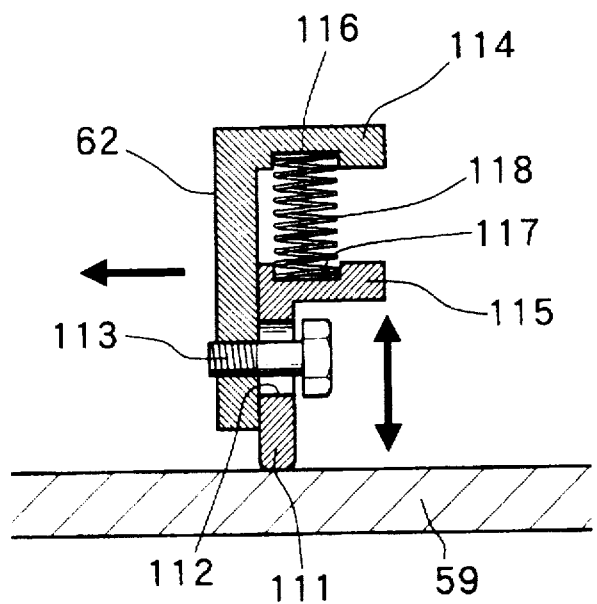
FIG. 9 is a section view of a blade equipped with a sliding plate showing a second embodiment of the present invention.
Figure 10:
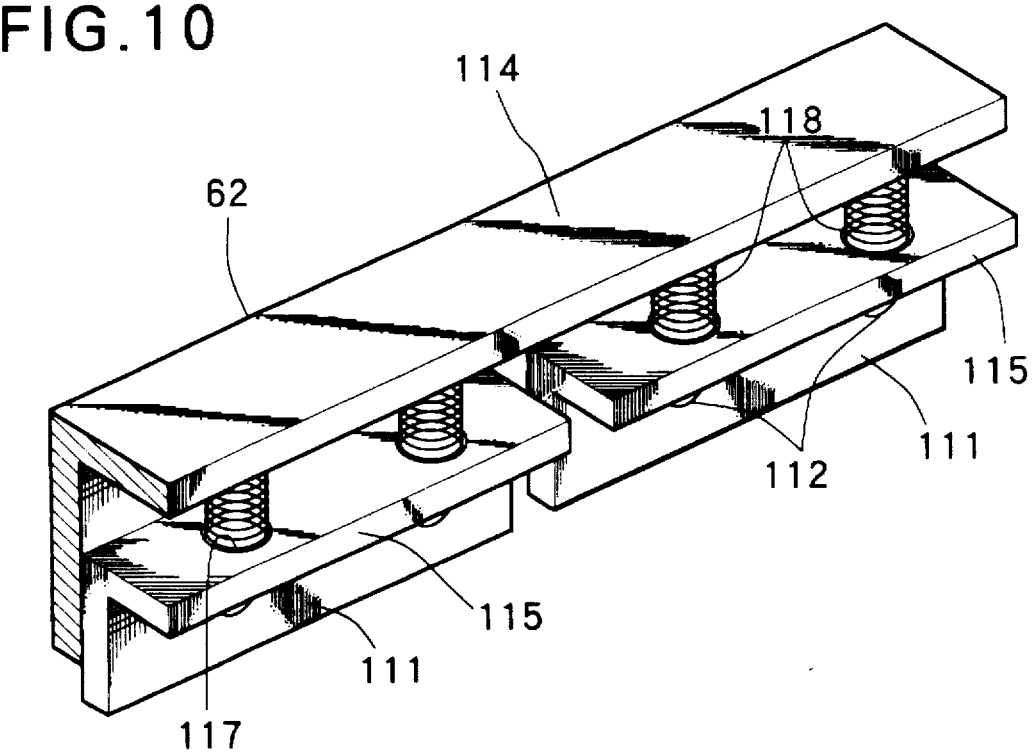
FIG. 10 is a perspective view partly in section of the blade equipped with the sliding plate of the second embodiment of the present invention.

FIGS. 9 and 10 show a second example of this invention, wherein the same parts as those of the first example are represented by the same reference numerals thereby omitting the detailed explanation thereof. This example illustrates a modification of the sliding member. Referring to FIGS. 9 and 10, the sliding member comprises a sliding plate 111 formed of stainless steel or steel and extended in the perpendicular direction. A plurality of oblong holes 112 extended in the perpendicular direction are formed in the sliding plate 111. This sliding plate 111 is mounted on the lower portion of the blade 62 in such a manner that the sliding plate 111 is free to move up and down in relation to the blade 62 by inserting a bolt 113 into each of the oblong holes 112. A plurality of the sliding plates 111 are mounted in the same manner as explained above along the full length of the blade 62 with a space being kept between the neighboring sliding plates 111. Therefore, each of the sliding plates 111 is capable of tilting inwardly along its length and in a direction opposite to each other. In the example shown in these Figs., these sliding plates 111 are movably mounted on the rearward side, in the rotational direction, of the blade 62. The blade 62 is provided at the top thereof with a rearwardly extending mounting member 114, and the sliding plate 111 is also provided at the top thereof with a rearwardly extending mounting member 115. Cylindrical mounting grooves 116 and 117 are formed on the lower side of the mounting member 114 and the upper side of the mounting member 115 respectively to face to each other. A coil spring 118 as a resilient member is mounted between the mounting grooves 116 and 117 as shown in FIG. 9. Each coil spring is located to correspond to the location of the oblong hole 112. This coil spring may be omitted if not required.

In this example, the blade 62 is provided with the sliding plate 111 which is adapted to slide on the heating plate 59, so that a portion of the soil left remained between the rotating blade 62 and the heating plate 59 can be removed by this sliding plate 111 sliding on the upper surface of the heating plate 59, thus avoiding the soil from being left on the upper surface of the heating plate 59 thereby performing the sterilization of the soil.

Since a plurality of the sliding plates 111 are mounted along the full length of the blade 62 so as to allow each of the sliding plates 111 to tilt freely, each of the sliding plates 111 can be slid in conformity with the surface condition of the heating plate 59. Further, since the coil spring 118 is mounted so as to press the sliding plate 111 toward the upper surface of the heating plate 59, the lower edge of the sliding plate 111 can be closely contacted with the upper surface of the heating plate 59. Further, when the lower edge of the sliding plate 111 is rounded as shown in FIG. 9, the slide resistance of the sliding plate 111 can be minimized.

Figure 11:
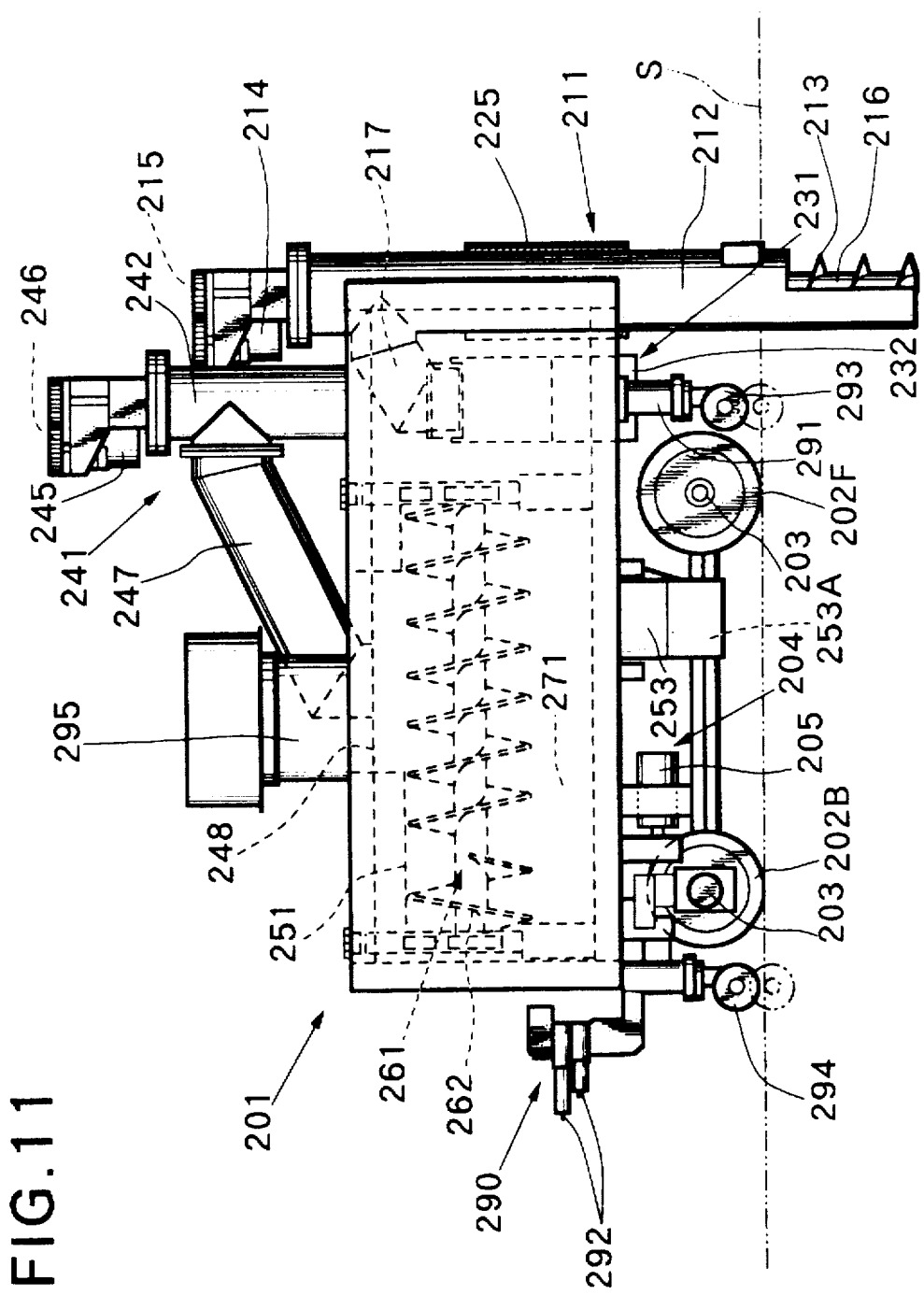
FIG. 11 is a side view partly in section showing a third embodiment of a cleaning sterilization apparatus for topsoil of the present invention.
Figure 19:
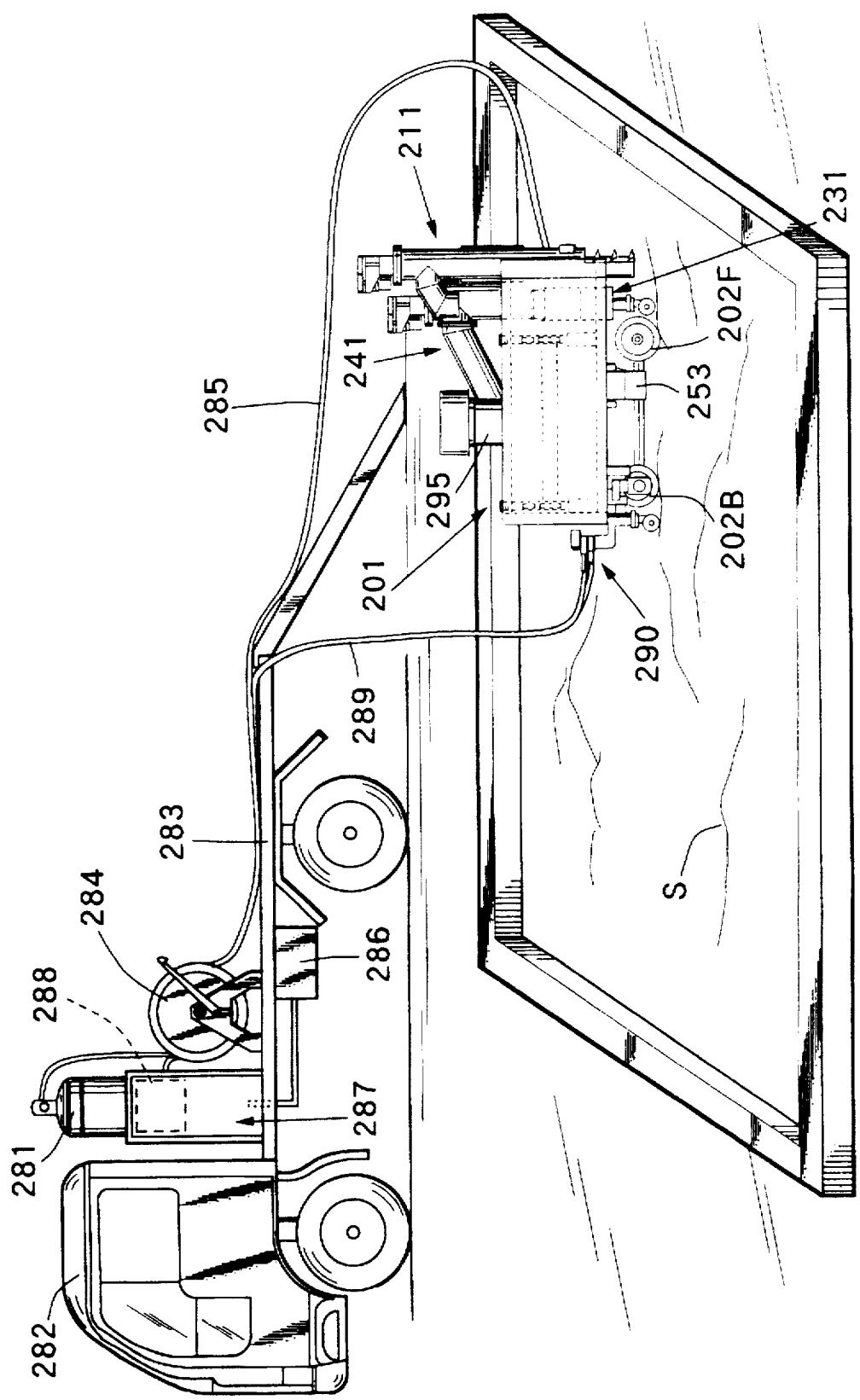
FIG. 19 is a view of the third embodiment of the present invention in operation.

FIGS. 11 and 19 illustrate a third example of this invention, wherein a pair of front wheels 202F and a pair of rear wheels 202B are rotatably attached to a pair of traveling shafts 203 respectively. A driving apparatus 204 for driving the traveling shafts 203 is mounted on one side of the traveling shafts 203 bearing the rear wheels 202B. This driving apparatus 204 is provided with an oil pressure motor 205 having a worm (not shown) fixed to the driving shaft of the pressure motor 205, the worm being engaged with a wheel (not shown) of the traveling shaft 203.

Figure 12:
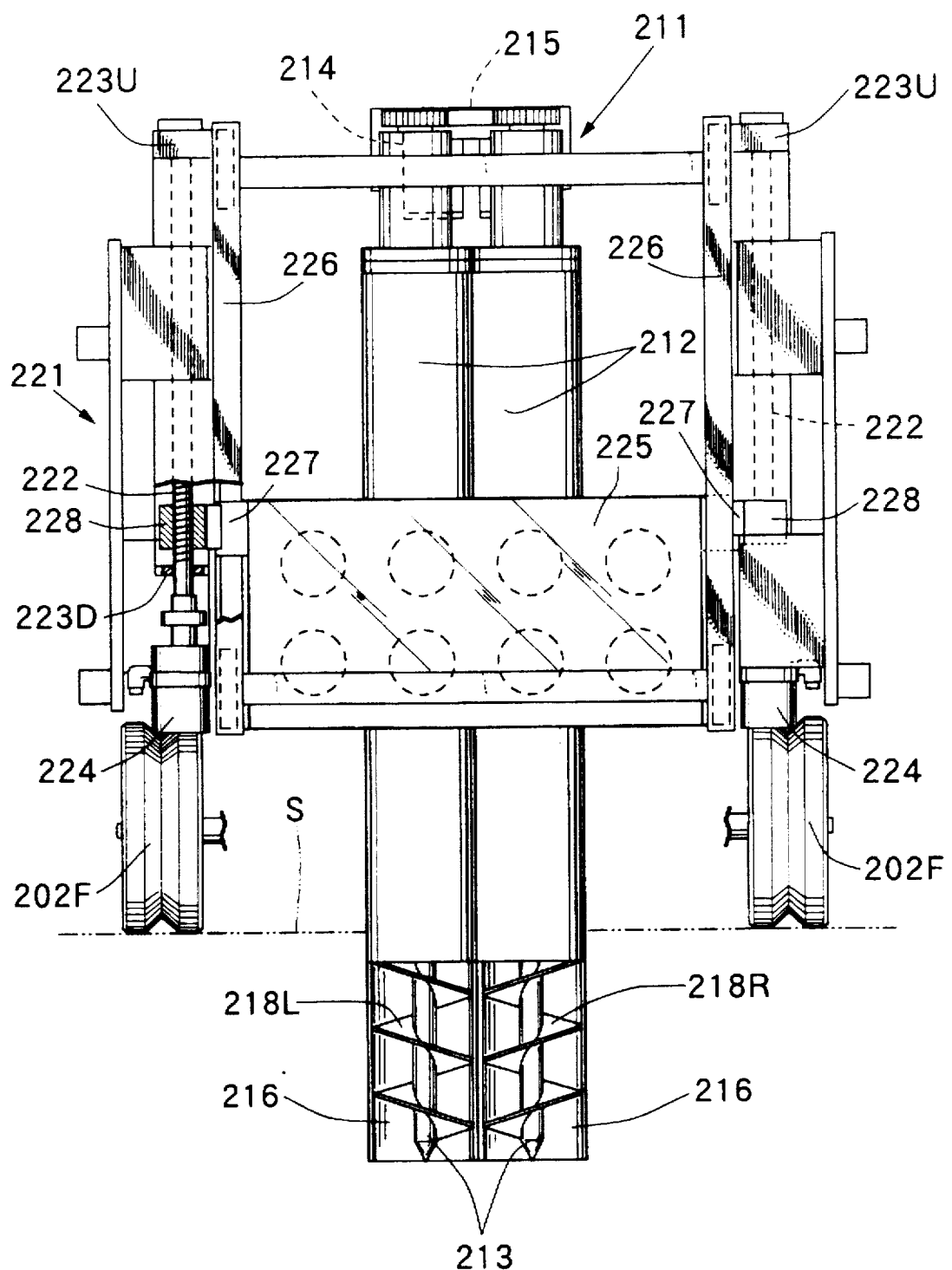
FIG. 12 is a front view of the intake equipment of the third embodiment of the present invention.

The intake apparatus 211 for taking up a topsoil into the apparatus body 201 is perpendicularly mounted on the front portion of the apparatus body 201. This intake apparatus 211 comprises a cylindrical body 212 and a screw conveyor 213 housed in the cylindrical body 212 as shown in FIG. 12. This screw conveyor 213 is adapted to be rotated via a set of gears 215 by an intake oil pressure motor 214 mounted on the upper portion of the cylindrical body 212. The lower end of the cylindrical body 212 is opened and at the same time a half of the lower forward end portion thereof is also opened thereby forming an intake port 216. The rear side of the upper portion of the cylindrical body 212 communicates with a curved pipe 217 inclined by an angle of 90 degrees. In the example shown in the drawing, a pair of parallel cylindrical bodies 212 are disposed, and vanes 218R and 218L of screw conveyors 213 are spirally formed in opposite directions from each other.

The intake apparatus 211 is mounted via an elevation apparatus 221 on the apparatus body 201. This elevation apparatus 221 comprises a pair of screw bars 222 disposed on left and right sides of the apparatus body 201. The screw bars 222 are respectively rotatably secured to the apparatus body 201 with its upper and lower end portions being secured by upper and lower bearings 223U and 223D fixed to the apparatus body 201. The lower end portion of each screw bar 222 is connected with an oil pressure motor 224 fixed to the apparatus body 201. A frame-like elevating body 225 is disposed between the pair of the screw bars 222, and adapted to move up and down along the guide members 226 disposed on the left and right sides of the apparatus body 201. The intake apparatus 211 is secured to the elevating body 225, and a pair of connecting arms 227 are fixed respectively to the upper left and right sides of the elevating body 225. Each of the connecting arms 227 is rotatably connected to a nut 228 screwed in the screw bars 222. Therefore, when the elevation oil pressure motors 224 are actuated to rotate the screw bars 222, the nuts 228 screwed in the screw bars 222 are caused to move up and down, thus causing the intake apparatus 211 fixed to the elevating body 225 to move up and down. When the intake apparatus 211 is positioned at its ascended position, the lower end of thereof is raised higher than the lowermost portion of the front wheel 202F, and when the intake apparatus 211 is positioned at its descended position, the lower end of thereof is inserted down into the soil "S" to a depth of about 40 cm, the intake port 216 being completely buried in the topsoil.

Figure 13:
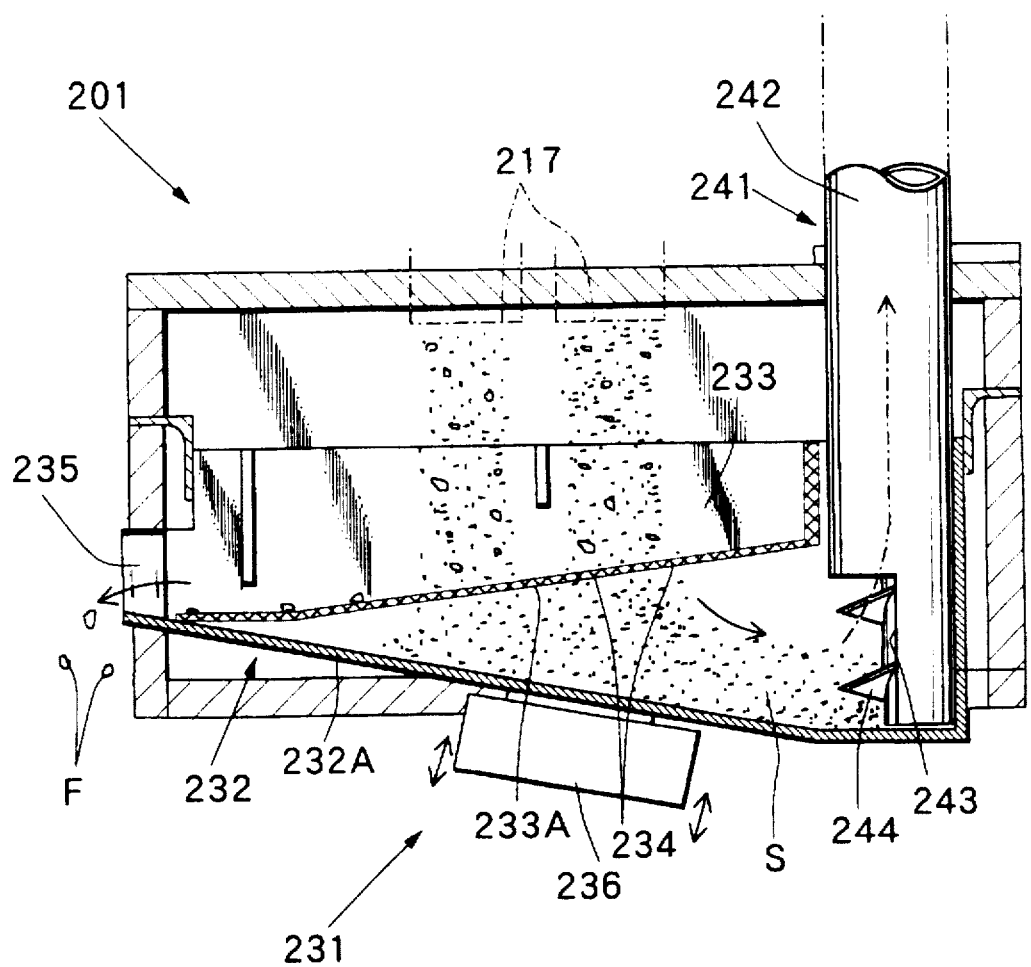
FIG. 13 is a section view of the separation equipment of the third embodiment of the present invention.

The apparatus body 1 is also provided with a separating apparatus 231 disposed below the lower opening of the curved pipe 217 of the intake apparatus 211. This separating apparatus 231 comprises as shown in FIG. 13 a box 232 having an open top elongated widthwise and an inclined separating passage 233. The inclined separating passage 233 is provided with a separating plate 233A which is inclined down leftward and provided with a plurality of separating openings 234. For example, the separating plate 233A is constituted by a metal mesh forming a sieve. On the left wall of the box 232 is formed an impurity discharge port 235 communicating with the inclined separating passage 233. Below the lower portion of the separating passage 233, there is disposed the bottom plate 232A of the box 232, which is inclined down rightward. A vibrating apparatus 236 is disposed below the bottom plate 232A. The separating plate 233A and the bottom plate 232A are adapted to be vibrated by this vibrating apparatus 236. The mesh size of the separating openings 234 is so controlled as to allow the soil "S" and sand to pass therethrough. At the right side of the bottom plate 232A constituting lower bottom, there is disposed the lower end portion of an injection apparatus 241.

Figure 14:
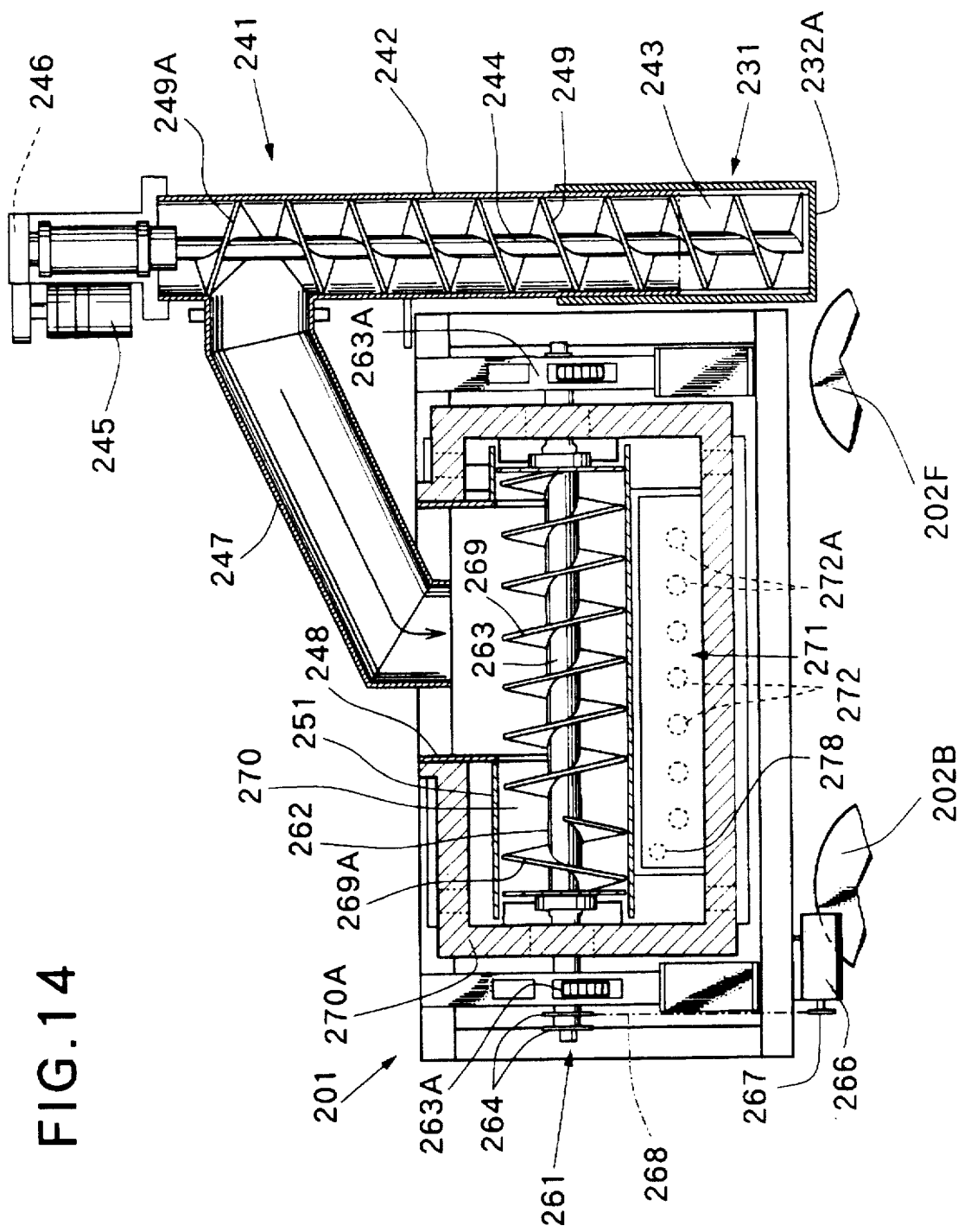
FIG. 14 is a longitudinal section view of the third embodiment of the present invention.

This injection apparatus 241 comprises a cylindrical body 242 vertically disposed and fixed to the apparatus body 201, and a suction screw conveyor 244. The cylindrical body 242 is provided at its lower end with a suction port 243 disposed on the right side of the bottom plate 232A. This screw conveyor 244 is adapted to be rotated via a set of gears 246 by an intake oil pressure motor 245 mounted on the upper portion of the cylindrical body 242. The rear side of the upper portion of the cylindrical body 242 communicates with a curved pipe 247 inclined by an angle of 90 degrees. The lower end of the curved pipe 247 is inserted into the injection port 248 opened to the upper portion of the apparatus body 201. Further, as shown in FIG. 14, the suction screw conveyor 244 is provided with a main vane portion 249 spirally formed in the same direction beginning from the lower end thereof ending to the location where the curved pipe 247 is connected, and at the same time provided, at its upper portion higher than the location where the curved pipe 247 is connected, with a reverse vane portion 249A spirally formed in a direction opposite to that of the main vane portion 249. Accordingly, when the intake oil pressure motor 245 is actuated to rotate the main vane portion 249, the soil "S" is transferred upward reaching to the location where the curved pipe 247 is connected, and then the ascending movement of the soil is suppressed by the reverse vane portion 249A and guided to move toward the curved pipe 247. By the way, the aforementioned intake screw conveyor 213 is also provided with the reverse vane portion at a location higher than its connecting portion with the curved pipe 217 in addition to the main vane portion which is mounted at a location lower than its connecting portion with the curved pipe 217.

Figure 15:
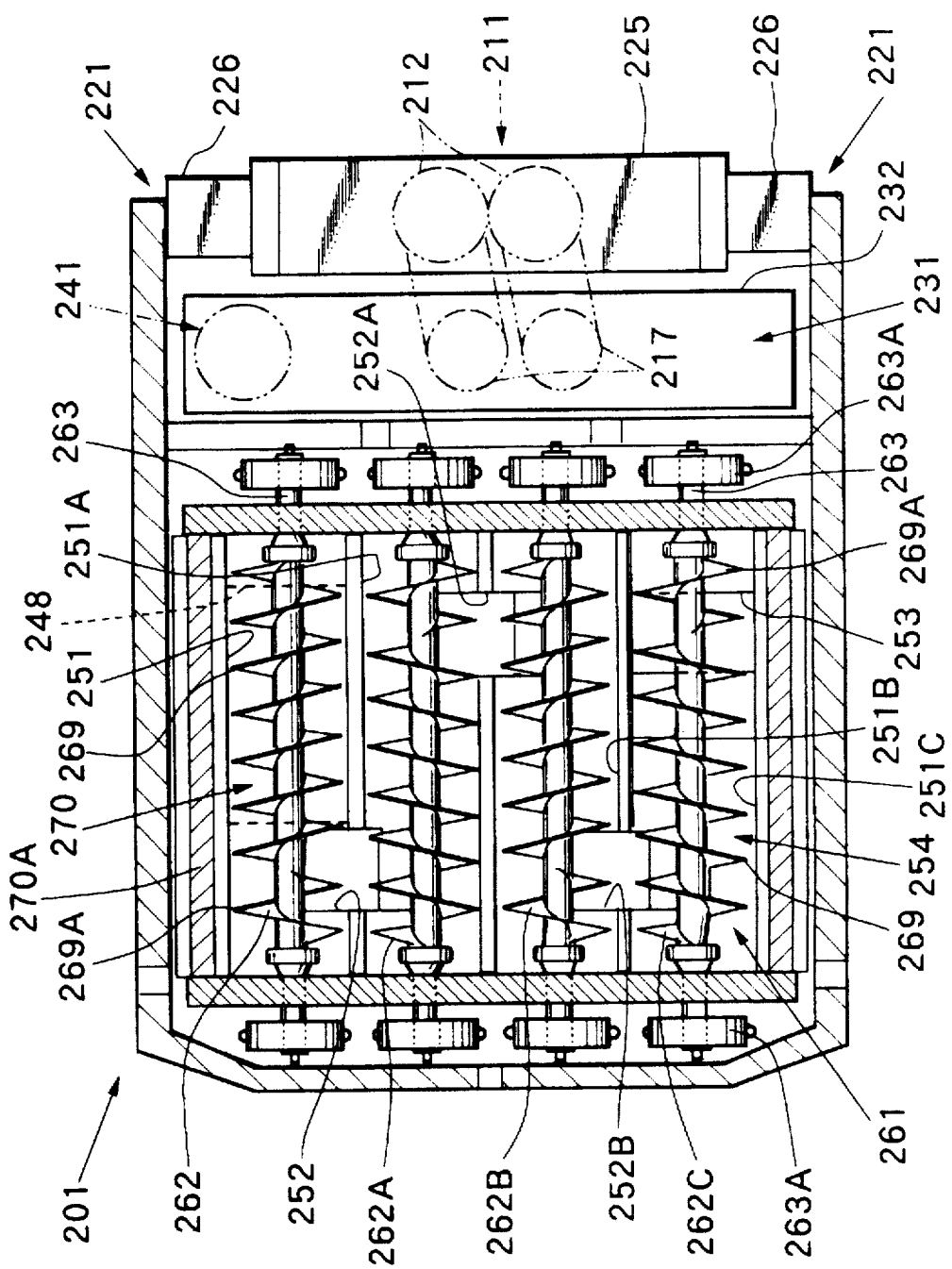
FIG. 15 is a horizontal section view of the third embodiment of the present invention.
Figure 16:
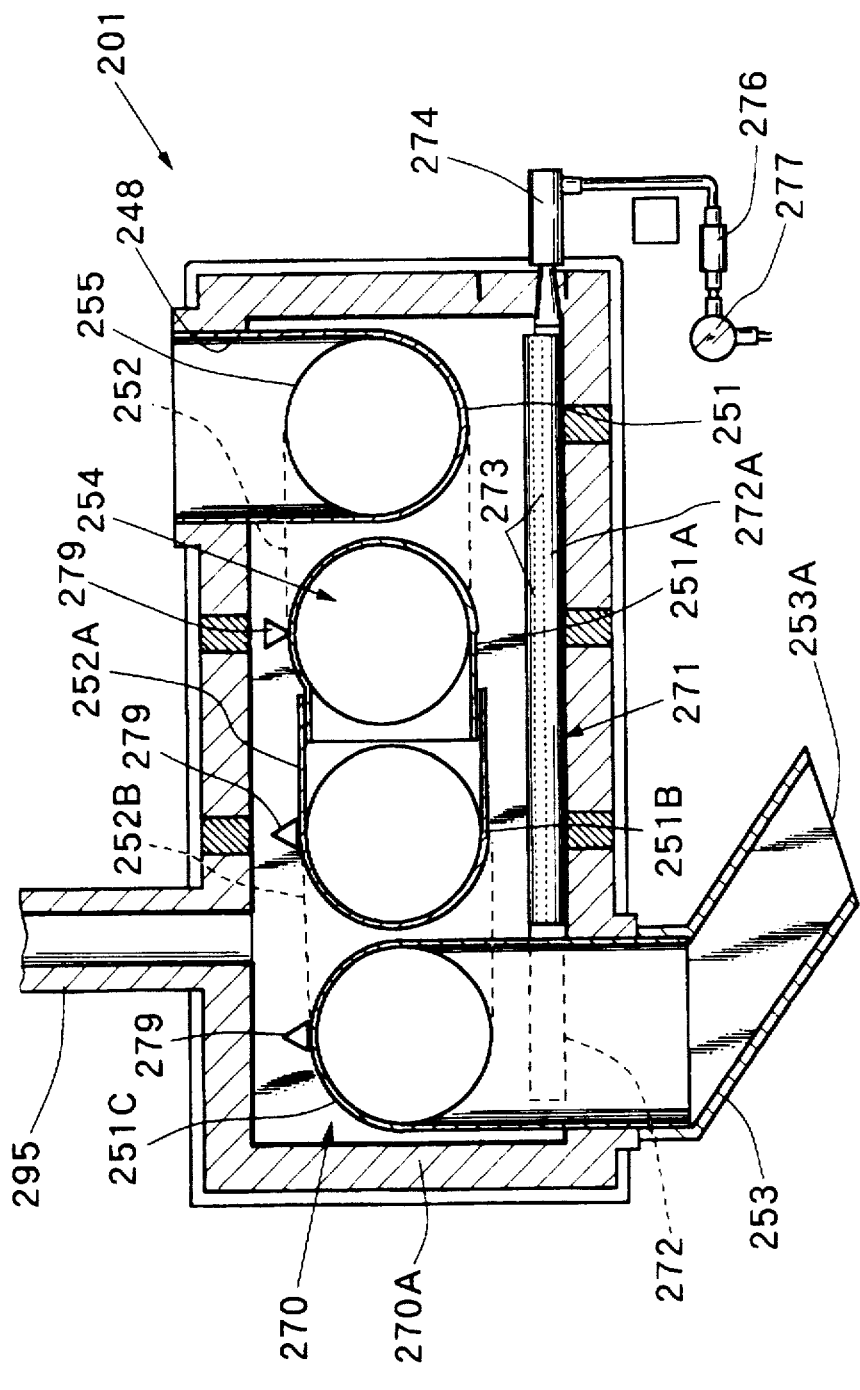
FIG. 16 is a longitudinal section view of the heating sterilization equipment of the third embodiment of the present invention.

As shown in FIGS. 14 to 16, the apparatus body 201 is provided therein with a first, second, third and fourth soil transferring pipes 251, 251A, 251B and 251C which are arrayed in parallel with each other from left to right, the longitudinal direction of each being in parallel with the traveling direction of the apparatus body 201. These soil transferring pipes 251, 251A, 251B and 251C are made of steel (such as stainless steel) cylindrical pipe and both ends thereof are closed. The first and second soil transferring pipes 251 and 251A communicate via a connecting pipe 252 at the rear end sides thereof. The second and third soil transferring pipes 251A and 251B communicate via a connecting pipe 252A at the forward end sides thereof. The third and fourth soil transferring pipes 251B and 251C communicate via a connecting pipe 252B at the rear end sides thereof. The bottom of the forward end portion of the fourth soil transferring pipe 251C is connected with a discharge-guiding pipe 253 having a discharge port 253A disposed at the lower portion of the apparatus body 201. Each of the connecting pipes 252, 252A and 252B are also made of steel (such as stainless steel) cylindrical pipe. A labyrinth type transferring passage 254 in the form of maze is formed by these first, second, third had fourth soil transferring pipes 251, 251A, 251B and 251C, and by the connecting pipes 252, 252A and 252B communicating these soil transferring pipes. An opening 255 is formed at the upper portion of the first soil transferring pipes 251 to communicate with the injection port 248. Further, as shown in FIG. 16, the first, second, third and fourth soil transferring pipes 251, 251A, 251B and 251C are inclined such that the left sides thereof are somewhat lowered.

The apparatus body 201 is further provided with a transferring apparatus 261 for transferring the soil "S" injected from the injection port 248 to the discharge port 253. This transferring apparatus 261 comprises a first, second, third and fourth screw conveyors 262, 262A, 262B and 262C each disposed inside the first, second, third and fourth soil transferring pipes 251, 251A, 251B and 251C; d pair of bearings 263A each bearing the both ends of the axial shaft 263 of each screw conveyor, a pair of sprockets 264 secured to the rear end of the axial shaft 263, a chain 265 wound between the pair of sprockets 264, a transferring oil pressure motor 266 disposed below the rear portion of the apparatus body 201 as shown in FIG. 14, and a drive transmitting chain 268 wound between the sprocket 267 mounted on the driving shaft of the transferring oil pressure motor 266 and the sprocket 264 of the first screw conveyor 262. As shown in FIG. 15, the first and third screw conveyors 262 and 262B are provided with a forward portion located at the upstream side of the connecting pipe 252 or 252B and with a rearward portion located opposite to the forward portion with both main vane 269 and reverse vane 269A, respectively. The second screw conveyor 262A is provided with a forward portion located at the upstream side of the connecting pipe 252A and with a rearward portion located opposite to the forward portion with both reverse vane 269A and main vane 269, respectively. The fourth screw conveyor 262C is provided with a forward portion located at the discharge port 253 and with a rearward portion located opposite to the forward portion with both reverse vane 269A and main vane 269, respectively. The spiral direction of the main vane 269 is opposite to that of the reverse vane 269A. Further, the spiral direction of the main vane 269 of the first and third screw conveyors 262 and 262B is opposite to that of the main vane 269 of the second and fourth screw conveyors 262A and 262C.

When the transferring oil pressure motor 266 is actuated, each of the screw conveyors 262, 262A, 262B and 262C is driven to rotate in the same direction with each other, thus transferring the soil "S" injected from the injection port 248 to the rear region of the first soil transferring pipe 251. Then, the soil is further transferred via the connecting pipe 252 to the forward region of the second soil transferring pipe 251A. After being passed through the second soil transferring pipe 251A, the soil is further transferred via the connecting pipe 252A to the rearward region of the third soil transferring pipe 251B. Then, after being passed through the third soil transferring pipe 251B, the soil is further transferred via the connecting pipe 252B to the rearward region of the fourth soil transferring pipe 251C. Furthermore, after being passed through the fourth soil transferring pipe 251C, the soil is further transferred via the discharge-guiding pipe 253 to the discharge port 253A from which the soil is allowed to fall at nearly the center of ground below the apparatus body 201. The soil transferring pipes 251, 251A, 251B and 251C as well as a thermal sterilization apparatus to be explained below are housed in a heating chamber 270 encircled by an insulating material 270A.

Figure 17:
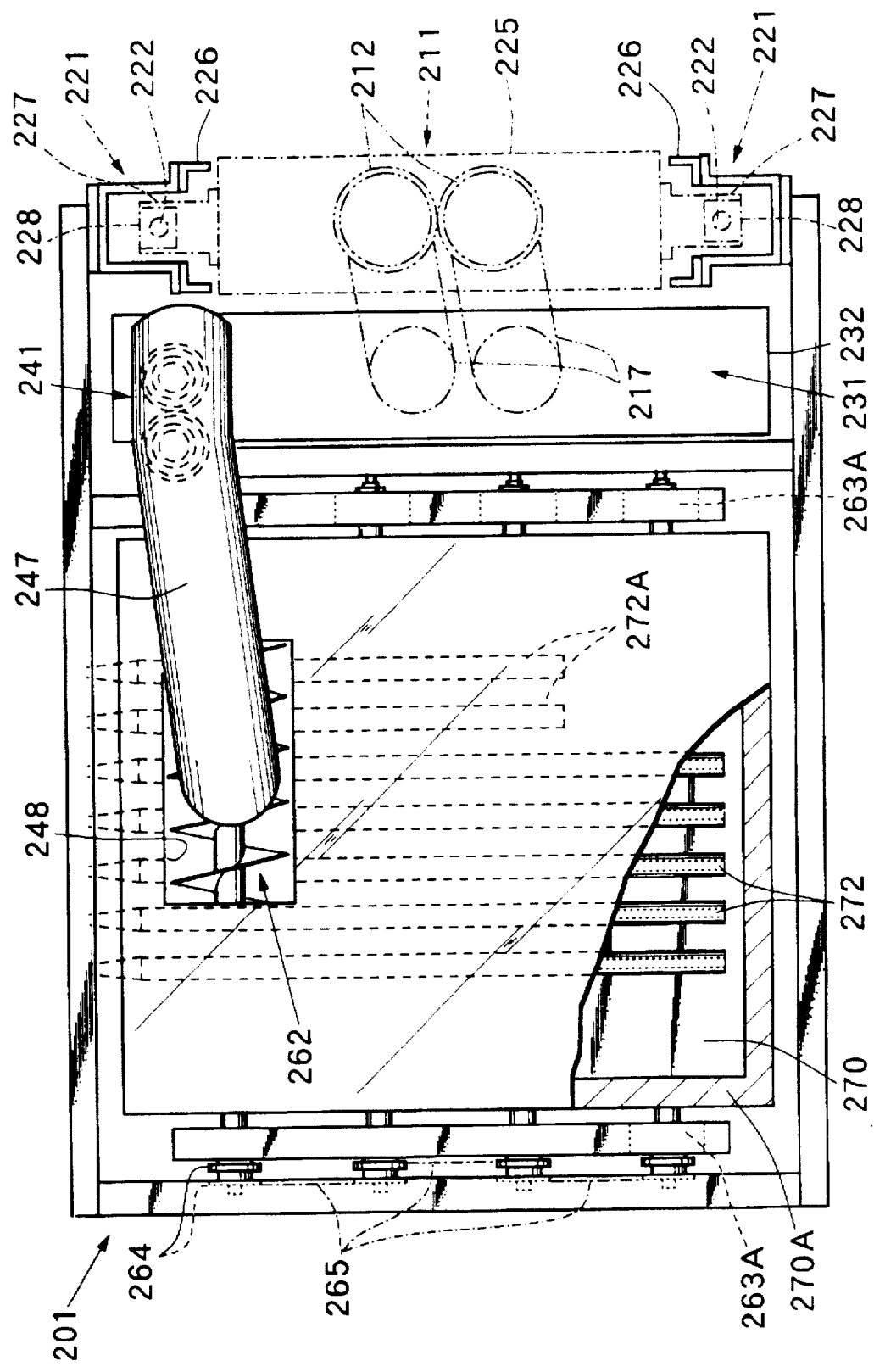
FIG. 17 is a plan view partly in section of a portion of the third embodiment of the present invention.
Figure 18:
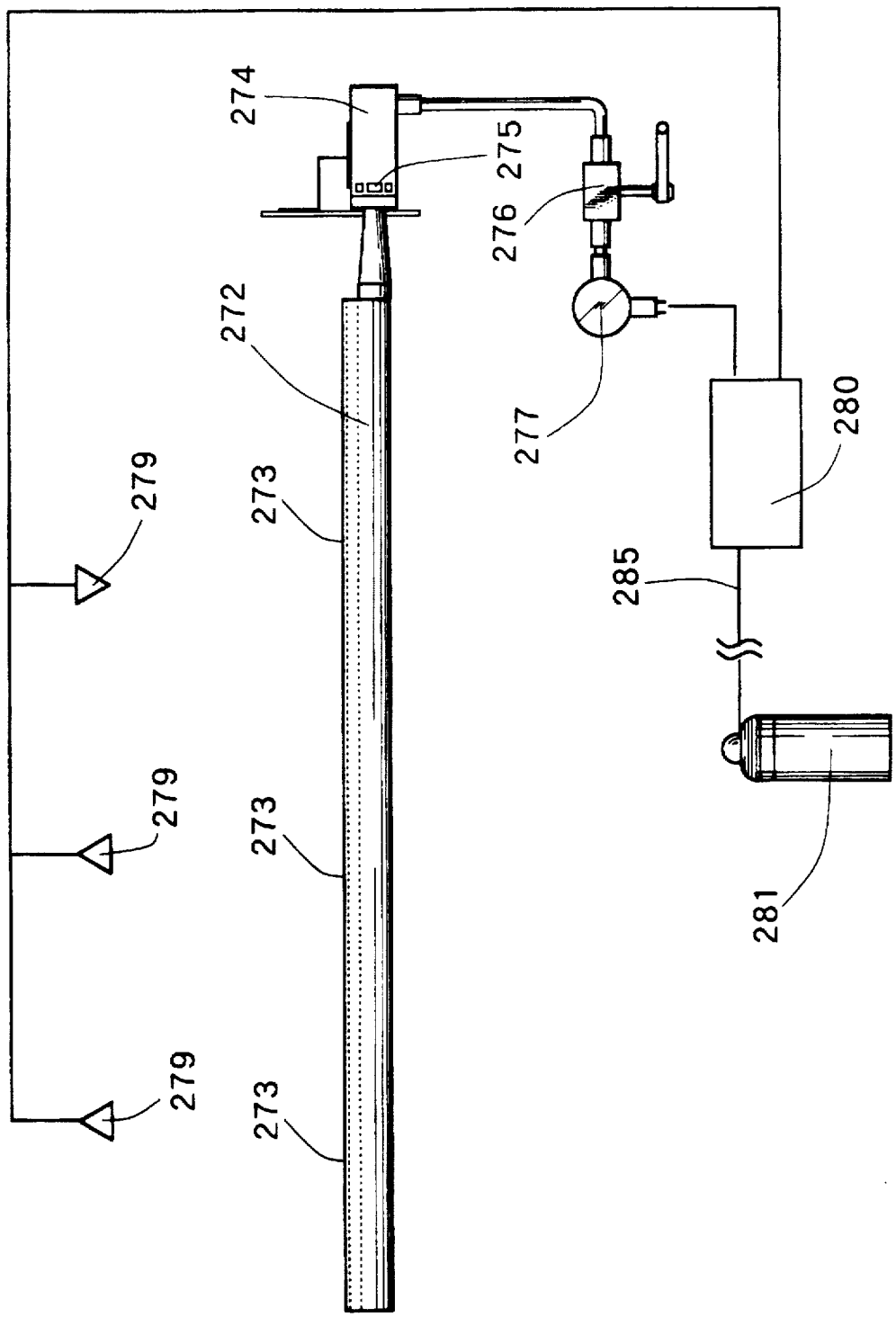
FIG. 18 is a side view of a gas burner of the third embodiment of the present invention.

Namely, the thermal sterilization apparatus 271 for thermally sterilizing the topsoil "S" is disposed below the soil transferring pipes 251, 251A, 251B and 251C. This thermal sterilization apparatus 271 comprises as shown in FIGS. 16 to 18 a plurality of gas burners 272 of long size and a plurality of gas burners 272A of short size, each gas burner being formed of stainless steel and arrayed in parallel with the longitudinal direction of the apparatus body 201. A plurality of flame ports are disposed underneath each of the soil transferring pipes 251, 251A, 251B and 251C. One end of each gas burners 272 and 272A is closed and the other end of each gas burners 272 and 272A is connected with a gas nozzle 274 to which an air supplying port 277 is attached. The gas nozzle 274 is connected via a switching valve 276 to a gas-supplying pipe 277. The reference numeral 278 in FIG. 14 represents a pilot burner for igniting the gas burner 272. As shown in FIG. 16, a temperature sensor 279 is provided at the upper portion of each soil transferring pipes 251, 251A, 251B and 251C. The gas-supplying pipe 277 as well as the pilot burner 278 are connected via a heat control apparatus 280 to an LPG gas cylinder 281. A temperature sensor 279 is electrically connected to the heat control apparatus 280 with which the ignition and extinguishing of the gas burner 272 are performed. The temperature of each soil transferring pipes 251, 251A, 251B and 251C is measured by the temperature sensor 279, and on the basis of the measured results, the flow rate and pressure of the gas to be supplied to the gas burners 272 and 272A are controlled to keep a predetermined temperature of these soil transferring pipes. The gas cylinder 281 can be mounted on the loading platform 283 of a vehicle 282 of two tons or so in carrying capacity. This gas cylinder 281 is connected via a gas hose pipe 285 of a hose reel 284 to the heat control apparatus 280 mounted on the apparatus body 201. On this vehicle 282 is further mounted a hydraulic pump 286 to be actuated by the rotation of the transmission of the vehicle 282. This hydraulic pump 286 is connected to an oil pressure control unit 287 mounted on the loading platform 283 of a vehicle 282. This oil pressure control unit 287 is provided with an oil pressure tank 288, which is connected a gas hose pipe 289 of a hose reel 284 to a connecting member 290 disposed at a rear portion of the apparatus body 201. On this connecting member 290 are mounted a plurality of connectors 292 corresponding in number with the hydraulic motors 205, 214, 224 and 266, and carriage elevation hydraulic cylinders 291. These connectors 292 are connected via a hydraulic circuit (not shown) to the hydraulic motors 205, 214, 224 and 266, and carriage elevation hydraulic cylinders 291. These carriage elevation hydraulic cylinders 291 are erected at the front portion of the front wheels 202F respectively. Supplementary elevation wheels 293 are rotatably (horizontally) provided under the carriage elevation hydraulic cylinders 291. When this carriage elevation hydraulic cylinders 291 is extended to lower the supplementary elevation wheels 293 down to the ground lower than the grounding level of the front wheel 202F, the apparatus body 201 can be steered with a small turning radius, since the supplementary elevation wheels 293 are rotatably (horizontally) mounted. Another pair of supplementary elevation wheels 294 are rotatably (horizontally) mounted at the real side of the rear wheels 201B and held higher than the rear wheels 201B. The supplementary elevation wheels 294 are adapted to be manually moved up and down as shown in FIG. 11 and the heights thereof are made adjustable by a fixing mechanism (not shown). The oil pressure control unit 287 is provided also with an operation device through which the hydraulic motors 205, 214, 224 and 266, and carriage elevation hydraulic cylinders 291 can be controllably driven, with the hydraulic pump 286 (mounted on the vehicle 282) being employed as a driving power. The reference numeral 295 represents a funnel erected on, and in communication with, the heating chamber 270.

Next, the method of using the cleaning sterilization apparatus mentioned above for cleaning and sterilizing a sand box court will be explained. First, a plurality of gas cylinders 281, the oil pressure control unit 287, the hose reel 284 and the apparatus body 201 are loaded on the loading platform 283 of a vehicle 282 as shown in FIG. 19. Upon reaching a sand box court to be cleaned, the apparatus body 201 is unloaded on the sand box court, and the hydraulic pump 286 is actuated by means of the transmission which is driven by the engine of the vehicle 282. Then, the oil pressure control unit 287 is actuated by using the hydraulic pump 286 as a motive power, thus successively actuating each hydraulic motor 205, 214, 224 and 226. Then, the elevation apparatus 221 is actuated to lower the elevating body 225 so as to force the intake port 216 to go into a soil "S" at a predetermined depth. The intake port 216 can be lowered to a predetermined level lower than the front wheel 202F in this manner when sand or soil is to be taken up. However, in the normal traveling state, the intake apparatus 211 can be raised as shown in FIG. 19 so that the intake apparatus 211 would not become any hindrance to the normal traveling operation. Then, the apparatus body 201 is allowed to travel forward by means of the crawlers 204 so as to take up the soil "S" from the intake port 216 by actuating the intake apparatus 211, and at the same time the intake screw conveyors 213 disposed on both sides are allowed to move upward for carrying the soil up to the curved pipe 217 from which the soil is allowed to fall down into the separating apparatus 231. In this case, as shown in FIG. 12, since the blades 218R and 218L of the intake screw conveyors 213 are spirally formed in the opposite direction from each other and the intake screw conveyors 213 rotate in the opposite direction from each other, the blades 218R and 218L are caused to rotate in the same speed with each other but in the opposite direction from each other. As result, the rotational resistance of the intake screw conveyors 213 are well balanced, thereby allowing the apparatus body 201 to stably travel in the straight direction. The amount of soil to be taken up by the intake port 216 can be adjusted by adjusting the height of the intake apparatus 211, by actuating the elevation equipment 221 and at the same time by adjusting the rotational speed per unit time of the screw conveyors 213. The soil "S"

discharged from the curved pipe 217 is then allowed to fall onto the separating plate 233A vibrating by means of the vibrator 236, the soil passed through the separating meshes 234 of the separating plate 233 is allowed to fall on the underlying bottom plate 232A, and the foreign matter "F" such as small stones and pieces of glass or large solid which are larger than the separating meshes 234 are removed out of the discharge port 235. Since the separating plate 233A is caused to vibrate by the vibrating apparatus 236, the clogging of the separating meshes 234 during the separating operation by the separating plate 233A can be avoided. The foreign matter "F" is then transferred via an inclined surface of the separating plate 233A to the discharge port 235. On the other hand, The soil thus passed through the separating plate 233A is transferred via the surface of the vibrating bottom plate 232A down to the suction port 243 of the injection apparatus 241.

The soil "S" separated from foreign matter "F" by means of the separating apparatus 231 is further transferred upward by means of the suction screw conveyor 244 from the suction port 243 of the injection apparatus 241 shown in FIG. 14, and then allowed to fall onto the injection pipe 248 after passing through the curved pipe 247. The soil "S" falling on the first soil transferring pipes 251 from the opening 255 disposed below the injection port 248 is transferred to the rear side by way of the first screw conveyor 262, i.e. the left side in FIG. 15. Then, the soil is further transferred via the connecting pipe 252 to the forward region of the second soil transferring pipe 251. After passing through the second soil transferring pipe 251A, the soil is further transferred via the connecting pipe 252A to the rearward region of the third soil transferring pipe 251B. Then, after passing through the third soil transferring pipe 251B, the soil is further transferred via the connecting pipe 252B to the rearward region of the fourth soil transferring pipe 251C. After passing through the fourth soil transferring pipe 251C, the soil is further transferred via the discharge-guiding pipe 253 to the discharge port 253A from which the soil is allowed fall at nearly the center of ground below the apparatus body 201. The soil "S" injected from the injection port 248 is thermally sterilized by the thermal sterilization apparatus 271 disposed below the labyrinth-type transferring passage 254 while the soil is transferred by the transferring apparatus 261 via the labyrinth-type transferring passage 254 to the discharge port 253A. This thermal sterilization apparatus 271 heat the soil "S" to a temperature of 150° to 200° C., for example, through the controlling action of the heat control apparatus 280. In this case, the temperature of each soil transferring pipes 251, 251A, 251B and 251C is measured by the temperature sensor 279, and on the basis of the measured results, the flow rate and pressure of the gas to be supplied to the gas burners 272 and 272A are controlled to keep a predetermined temperature of these soil transferring pipes. When the temperature is raised higher than the preset temperature, the on-off control of the gas supply is operated. In this case, since the heating by the thermal sterilization apparatus 271 is confined to the interior of the heating chamber 270 covered with a heat-insulating material "A", it is possible to achieve an excellent thermal efficiency and to prevent an increase in temperature of the external portion of the apparatus body 201. The soil "S" thus thermally sterilized is then discharged from the discharge port 253A directed toward the center portion underneath the apparatus body 1. Since the soil "S" taken up by the intake apparatus 211 mounted at the forward central portion of apparatus body 201 is discharged from the central portion of ground underneath the apparatus body 201, substantial leveling of soil after finishing the sterilization of the soil in the sand box court or farm land would not be required.

When a farm field such as a crop land is to be sterilized using this cleaning sterilization apparatus, the topsoil is taken up by the intake apparatus 211 in the same manner as explained above, and then after removing foreign matters "F" by the separating apparatus 231, the soil separated from the foreign matters "F" is sterilized while being transferred by the transferring apparatus 261 at a temperature of about 300° C., thereby killing any harmful bacteria contained in the topsoil. The sterilization of soil treated in this manner provides a farm land which is very advantageous in performing chemical-free cultivation.

In this example, the oil control unit 287 is constituted in separate from the apparatus body 201, and these structures are connected with the hydraulic hose pipe 289. Further, each apparatus is constructed to be driven by the hydraulic motors 205, 214, 224 and 266, and carriage elevation hydraulic cylinders 291. Therefore, it has become possible to minimize the width of the apparatus body 201 so as to be used at a narrow area. Furthermore, since each of the screw conveyors 213, 244, 262, 262A, 262S and 262C is provided with both a main vane portion and a reverse vane portion, the topsoil can be smoothly transferred in a direction approximately perpendicular to each of the screw conveyors 213, 244, 262, 262A, 262B and 262C. Further, since the separating apparatus 231 is provided with the vibrating apparatus 236, the separation of soil from foreign matter "F" and the transfer of soil can be smoothly performed. Moreover, since the transferring passage 254 is formed of labyrinth-type, a relatively long transfer passage 254 can be obtained even if the apparatus body itself is a box of small size and the thermal sterilization of the topsoil can be effectively carried out during the transfer of the topsoil through the labyrinth transfer passage 254. Since the first, second, third and fourth soil transferring pipes 251, 251A, 251B and 251C are constructed such that one end thereof facing the discharge guiding pipe 253 is somewhat inclined downward, the transfer of the topsoil between the soil transferring pipes can be smoothly carried out. Since the thermal sterilization apparatus 271 is constructed such that the temperature of each soil transferring pipe is measured by the temperature sensor 279, and on the basis of the measured results, the flow rate and pressure of the gas to be supplied to the gas burners 272 and 272A are controlled to keep a predetermined temperature of these soil transferring pipes, the topsoil can be thermally sterilized at a desired temperature, thus making it possible to control the heating temperature depending on the kinds of the bacteria, bacillus or eggs of ascarides to be killed. Therefore, it is possible to selectively sterilize the soil by only killing harmful bacteria.

Since supplementary elevation wheels 293 and supplementary wheels 294 are provided in free to move up and down at the lower portion of the apparatus body 201, the apparatus body 201 can be turned in a narrow area. Further, the soil transferring pipes 251, 251A, 251B and 251C are formed of steel pipe such as stainless steel pipe housing therein screw conveyors 262, 262A, 262B and 262C respectively, the soil transferring pipes 251, 251A, 251B and 251C being rotatably housed in the heating chamber 270. The rotation axis 263 for rotating each of these screw conveyors 262, 262A, 262B and 262c is extended through the wall of the heating chamber 270, and the external portion of the rotation axis 263 exposed out of the heating chamber 270 is provided with the sprocket 264A. Therefore, it is possible to prevent any of the bearing 263A, the sprocket 264 for transmitting the rotation of the hydraulic motor 266 and the chain 265 from being exposed to the heat from the thermal sterilization apparatus 271. As a result, it is possible to assure a stable operation of the transferring apparatus 261 for a long period of time. Moreover, since the transfer passage 54 is constituted by the cylindrical soil transferring pipes 251, 251A, 251B and 251C, the interior of each soil transferring pipe having a circular cross-section can be uniformly heated by the thermal sterilizing apparatus 271, and at the same time the soil "S" transferred by the screw conveyors 262, 262A, 262B and 262C can be concurrently agitated, thus realizing a uniform thermal sterilization.

Figure 20:
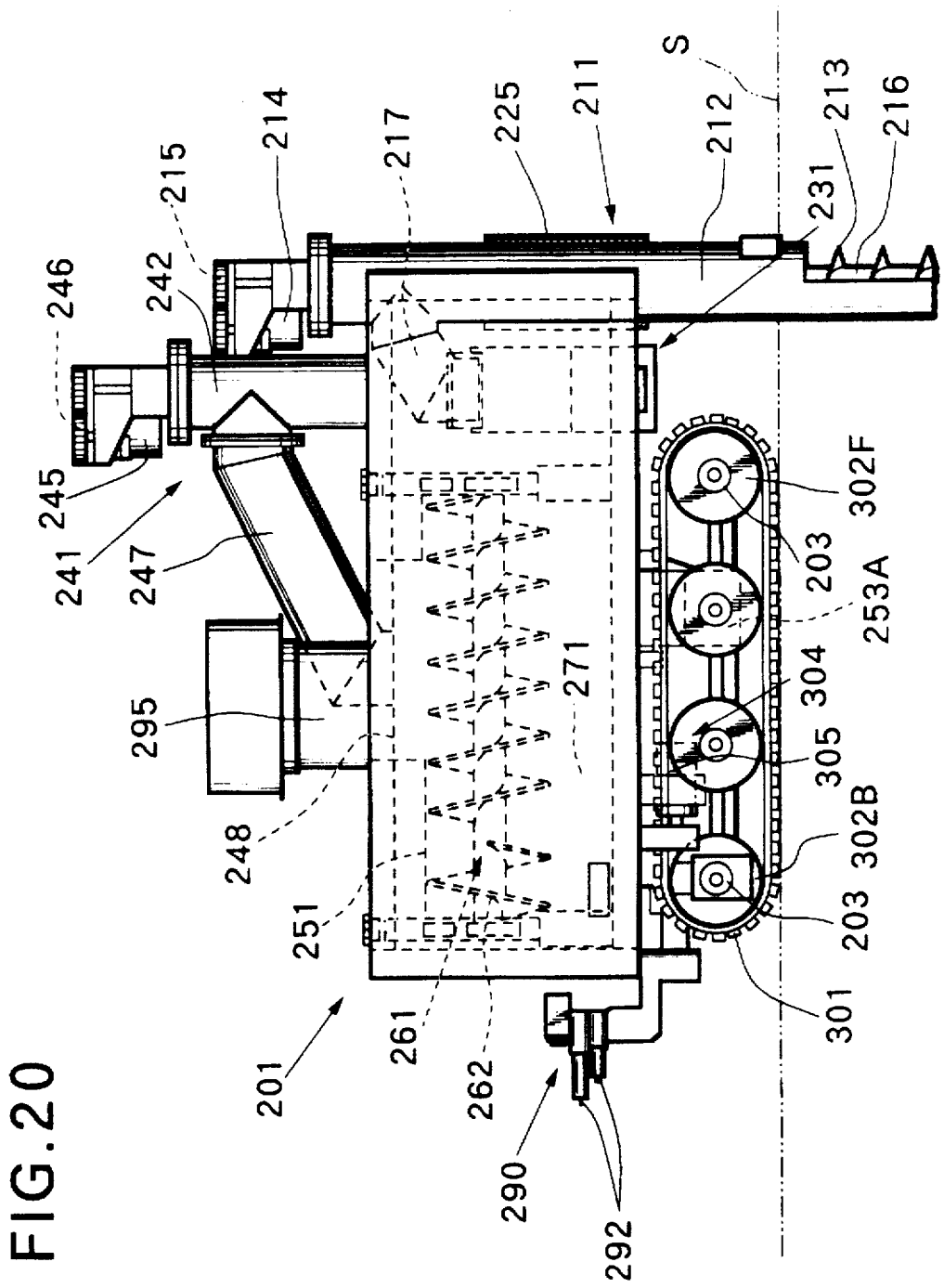
FIG. 20 is a section view partly in section showing a fourth embodiment.

FIG. 20 shows a fourth example wherein the same parts as those of the third example is represented by the same reference numerals thereby omitting the detailed explanation thereof. This example illustrates a structure where a crawler 301 is mounted on the apparatus body 201, and front wheels 302F and rear wheels 302B for the crawler are provided at the lower portion of the apparatus body 201. The travel-driving apparatus 304 is constructed such that the rear wheels 302B on both sides can be actuated by the hydraulic motors 305 disposed on both sides.

This invention is not limited to the above examples, but may be modified in various ways. For example, the travel driving apparatus, the intake apparatus, the elevation apparatus, the separation apparatus and the heating apparatus may be of any types other than explained above. In the above examples, the blades of each stage are fixed to the central axis and adapted to be rotated by the rotation of the central axis. However, the blades of each stage may be rotatably mounted around the central axis so that the blades of each stage can be rotated individually by a motive power transmitting means such as chain or gear. Further, in the above examples, each apparatus is shown to be actuated by an engine or a hydraulic motor, but it may be actuated by electric driving means or air pressure. Additionally, a tire may be employed for the traveling apparatus, and a bucket-type conveyor may be employed for the intake apparatus. It is also possible to employ an oil burner for the heating apparatus. As for the elevating apparatus, the intake apparatus may be designed to move up and down by means of a hydraulic cylinder. The number of the screw conveyors 13 is not restricted to two, but may be one, three, four or more. It is possible to control the volume of the topsoil to be taken up by adjusting the number of the screw conveyors 13. However, the number of the screw conveyors 13 should preferably be an even number, and the number of the screw conveyors having a reversibly directed spiral vane should also be the same as the number of the screw conveyors having a normally directed spiral vane in order to assure a balance in rotational resistance. Further, the number of the suction screw conveyors of the injection apparatus may be two or more. In the second example, a coil spring is employed, but it may be omitted so as to allow the sliding plate 111 to slide along the surface of the heating plate, while applying its own weight onto the surface of the heating plate. In the second example, a plurality of sliding plates separated from each other are employed, but only a single sliding plate having the same length as that of the blade may be employed instead of the aforementioned divided sliding plates. A flat spring may be employed in place of the aforementioned coil spring 118.

I claim:

1. A cleaning sterilization apparatus for topsoil which comprises:

an apparatus body having a lower portion with means for traveling over a ground surface;

a driving means mounted on said apparatus body, for driving said means for traveling;

an intake means positioned at a forward side of said apparatus body, for taking up the topsoil into the apparatus body;

a separating means provided in said apparatus body for separating and removing foreign matter from the soil taken up by the intake means;

a heat sterilization means provided in said apparatus body for thermally sterilizing the topsoil separated by the separating means; and, a discharge port provided in said apparatus body for discharging the sterilized topsoil out of the apparatus body;

wherein said intake means further comprises:

at least one screw conveyor having an elongated cylindrical body, said cylindrical body having a lower end side wall with a portion that is open in a forward direction of travel for the apparatus to form a topsoil intake port, said screw conveyor also having a spiral vane mounted for rotation around an axis extending longitudinally through said cylindrical body, said spiral vane extending to the intake port for contact with the topsoil, and said screw conveyor having a motor for rotating said spiral vane while in contact with the topsoil to convey topsoil upward; and elevation equipment provided at a front side of said apparatus body for moving said intake screw conveyor axially and substantially vertically downward into the topsoil, said elevation equipment also being operable for moving the intake screw conveyor upward and out of the topsoil.

2. A cleaning sterilization apparatus according to claim 1, wherein two screw conveyors are provided, said screw conveyors being paired and mounted to said elevation equipment, the screw conveyors having first and second respective spiral vanes spirally directed in opposite directions relative to each other, and wherein said first spiral vane is rotated in one rotational direction and wherein said second spiral vane is rotated in a second rotational direction opposite the first rotational direction while the topsoil is conveyed upwardly by the respective conveyors.

3. A cleaning sterilization apparatus according to claim 1, wherein said separating means is provided with a sieve and with a vibrating means for vibrating the sieve.

4. A cleaning sterilization apparatus according to claim 3, which further comprises a crushing means for crushing the topsoil taken up by the intake port, said crushing means crushing clods included in the topsoil prior to sieving the same with the use of said sieve.

5. A cleaning sterilization apparatus for topsoil which comprises:

an apparatus body provided at its lower portion with means for traveling over a ground surface;

a driving means mounted on said apparatus body, for driving said means for traveling;

an intake means provided at a forward side of said apparatus body, for taking up the topsoil into the apparatus body;

a separating means provided in said apparatus body for separating and removing foreign matter from the soil taken up by the intake means;

a heat sterilization means provided in said apparatus body for thermally sterilizing the topsoil separated by the separating means, and a discharge port provided in said apparatus body for discharging the sterilized topsoil out of the apparatus body, wherein said heat sterilization apparatus further comprises:

a heating chamber provided in said apparatus body;

a plurality of heating compartments provided inside said heating chamber, each of said heating compartments being approximately cylindrical in shape for receiving the topsoil and each of said heating compartments having a bottom and a heating plate disposed horizontally at said bottom;

a central axis vertically provided at the center of each heating plate;

a plurality of blades radially extending from said central axis and adapted to rotate around said central axis and along an upper surface of each heating plate;

rotating means for rotating the blades to convey the topsoil along the upper surface of each heating plate;

heating means for heating a lower surface of each heating plate; and a port being provided in each heating plate for allowing the topsoil heated by said heating plate to drop therethrough.

6. A cleaning sterilization apparatus according to claim 5, wherein said central axis is rotatably provided within said heating chamber, and around and coaxially with said central axis is provided an inner cylinder at a center of said heating plates, said inner cylinder extending upward, and wherein each of said blades is provided at a proximal end thereof with a portion secured to the central axis, and wherein said rotating means further comprises a motor.

7. A cleaning sterilization apparatus according to claim 5, wherein said heating chamber is provided therein with said heating compartments formed in multiple stages from an uppermost heating compartment to a lowermost heating compartment, and wherein said heating means further comprises at least one burner disposed below the lowermost heating compartment.

8. A cleaning sterilization apparatus according to claim 7, wherein said at least one port in each respective heating plate is disposed one revolution of said blades less one port position from the port immediately above each respective heating plate.

9. A cleaning sterilization apparatus according to claim 5, wherein said blades are each provided with a sliding member adapted to slide on an upper surface of the heating plate.

10. A cleaning sterilization apparatus according to claim 9, wherein said sliding member includes a brush.

11. A cleaning sterilization apparatus according to claim 8, wherein each of said compartments is partitioned by a divider plate with an outer circumference thereof being contacted by an inner surface of said heating chamber to be fixed thereto without any gap, said divider plate having a hot air hole in a center of said divider plate, wherein one of said heating compartments is positioned above said divider plate, wherein one of said heating compartments is positioned below said divider plate, and wherein said hot air hole in the center of said divider plate provides communication between said one of said heating compartments positioned above said divider plate, and said one of said heating compartments positioned below said divider plate.

12. A cleaning sterilization apparatus according to claim 1, wherein said heat sterilization means comprises:

a heating chamber provided in said apparatus body;

a plurality of cylindrical bodies for conveying the topsoil, said cylindrical bodies being laterally disposed in parallel in said heating chamber;

a spiral vane rotatably provided in each of said cylindrical bodies;

rotating means for rotating said spiral vane in each of said cylindrical bodies, wherein each spiral vane is so formed and rotated, so as to convey the topsoil in opposite longitudinal directions with respect to the adjacent cylindrical bodies; and heating means for heating outer surfaces of said cylindrical bodies, wherein a first one of said adjacent cylindrical bodies discharges topsoil to a second one of said adjacent cylindrical bodies towards one end of said first and second adjacent cylindrical bodies, and wherein said second one of said adjacent cylindrical bodies receives the topsoil and conveys the topsoil to an opposite end for transfer to a next adjacent cylindrical body.

13. A cleaning sterilization apparatus according to claim 12, wherein said adjacent spiral vanes have at least respective portions formed to spiral in opposite rotational directions, and wherein said rotating means is operable for rotating said spiral vane in each of said cylindrical bodies in the same rotational direction, for conveying the topsoil in opposite longitudinal directions in said adjacent cylindrical bodies, and wherein said heating means comprises a plurality of burners, said plurality of burners being disposed below said plurality of cylindrical bodies within said heating chamber.

* * * * *